US010421806B2

(12) United States Patent
Riazi et al.

(10) Patent No.: US 10,421,806 B2
(45) Date of Patent: Sep. 24, 2019

(54) ANTI-SALMONELLA ANTIBODIES AND USES THEREOF

(71) Applicant: ABCELEX TECHNOLOGIES INC., Ontario (CA)

(72) Inventors: Ali Riazi, Ontario (CA); Rashida Williams, Ontario (CA); Dea Shahinas, Ontario (CA); Saeid Babaei, Ontario (CA); Zhun Yan, Ontario (CA)

(73) Assignee: ABCELEX TECHNOLOGIES INC., Ontario (CA)

(*) Notice: Subject to any disclaimer, the term of this patent is extended or adjusted under 35 U.S.C. 154(b) by 0 days.

(21) Appl. No.: 15/548,759

(22) PCT Filed: Feb. 3, 2016

(86) PCT No.: PCT/IB2016/050546
§ 371 (c)(1),
(2) Date: Aug. 3, 2017

(87) PCT Pub. No.: WO2016/125089
PCT Pub. Date: Aug. 11, 2016

(65) Prior Publication Data

US 2018/0030120 A1 Feb. 1, 2018

Related U.S. Application Data

(60) Provisional application No. 62/112,035, filed on Feb. 4, 2015.

(51) Int. Cl.

*C07K 16/12* (2006.01)
*G01N 33/569* (2006.01)
*A61K 35/66* (2015.01)
*A61K 39/40* (2006.01)
*A61K 45/06* (2006.01)
(Continued)

(52) U.S. Cl.
CPC .......... *C07K 16/1235* (2013.01); *A61K 35/66* (2013.01); *A61K 39/40* (2013.01); *A61K 45/06* (2013.01); *C07K 16/005* (2013.01); *C12N 7/00* (2013.01); *G01N 33/56916* (2013.01); *C07K 2317/22* (2013.01); *C07K 2317/565* (2013.01);
(Continued)

(58) Field of Classification Search
CPC .......... G01N 33/56916; C07K 16/1235; C07K 2317/22; C07K 2317/569; C07K 2317/76; C07K 2317/94; C07K 2317/565; C07K 16/005; C12N 7/00; A61K 39/40; A61K 35/66; A61K 45/06
See application file for complete search history.

(56) References Cited

PUBLICATIONS

Nowacka, A., "Isolation of *Salmonella* Serovar-Specific SingleDomain Antibodies", A Thesis Presented to The University of Guelph, Ontario, Canada, Sep. 30, 2014 (Sep. 30, 2014). (Year: 2014).*
(Continued)

*Primary Examiner* — Jana A Hines
(74) *Attorney, Agent, or Firm* — Intellectual Property Law Group LLP

(57) ABSTRACT

The present disclosure provides anti-*Salmonella* antibodies or antibody fragments, such as camelid single domain antibodies (VHHs), along with associated nucleic acids, host cells and phages. Methods of reducing the presence of *Salmonella* in an animal or an animal environment, methods and formulations for treating *Salmonella* infection, and methods of detecting *Salmonella* are also described.

1 Claim, 14 Drawing Sheets

Specification includes a Sequence Listing.

4E08

Polypeptide sequence (SEQ ID NO:1):
HVQLVESGGGLVQAGGSLRLSCAASGLDFSSYAMGWFRQAPGEEREYVAGISRFGGRLYYADSVKGRFTISRDNA
KNTVYLQMNSLKPEDTAIYHCAADRRSGLGTSKEYDYWGQGTQVTVSS

Nucleic acid sequence (SEQ ID NO:19):
CATGTGCAGCTGGTGGAGTCTGGGGGAGGATTGGTGCAGGCTGGGGGCTCTCTGAGACTCTCCTGTGCAGC
CTCTGGACTGGACTTCAGTAGCTATGCCATGGGCTGGTTCCGCCAGGCTCCAGGAGAGGAGCGTGAGTACGT
AGCAGGTATTAGTAGATTTGGTGGTAGGCTCTACTATGCAGACTCCGTGAAGGGCCGATTCACCATCTCCAGA
GACAACGCCAAGAACACGGTGTATCTGCAAATGAACAGTCTGAAACCTGAGGACACGGCCATTTATCACTGT
GCAGCCGATAGACGGTCGGGGTTGGGGACCAGTAAGGAGTATGACTACTGGGGCCAGGGGACCCAGGTCA
CCGTCTCCTCA

1E08

Polypeptide sequence (SEQ ID NO:2):
QVQLVESGGGLVQAGGSLRLSCAASGLDFSSYAMGWFRQAPGEEREYVAGISRFGGRLYYADSVKGRFTISRDNA
KNTVYLQMNSLKPEDTAIYHCAADRRSGLGTSKEYDYWGQGTQVTVSS

Nucleic acid sequence (SEQ ID NO:20):
CAGGCTCAGGTACAGCTGGTGGAGTCTGGGGGAGGATTGGTGCAGGCTGGGGGCTCTCTGAGACTCTCCTG
TGCAGCCTCTGGACTGGACTTCAGTAGCTATGCCATGGGCTGGTTCCGCCAGGCTCCAGGAGAGGAGCGTGA
GTACGTAGCAGGTATTAGTAGATTTGGTGGTAGGCTCTACTATGCAGACTCCGTGAAGGGCCGATTCACCATC
TCCAGAGACAACGCCAAGAACACGGTGTATCTGCAAATGAACAGTCTGAAACCTGAGGACACGGCCATTTAT
CACTGTGCAGCCGATAGACGGTCGGGGTTGGGGACCAGTAAGGAGTATGACTACTGGGGCCAGGGGACCCA
GGTCACCGTCTCCTCA

0A09

Polypeptide sequence (SEQ ID NO:3):
QVQLVESGGGLVQAGGSLRLSCAASGRSFSLYGMGWFRQAPEKEREFVAAISGSGLATSYVDSVKGRFTISRDNA
KNTVYLQMNSLKPEDTAVYYCAQRWTSGTIARATGEYGYWGQGTQVTVSS

Nucleic acid sequence (SEQ ID NO:21):
CAGGCTCAGGTACAGCTGGTGGAGTCTGGGGGAGGATTGGTGCAGGCTGGGGGGTCTCTGAGACTCTCCTG
TGCAGCCTCTGGACGCAGCTTCAGTCTTTATGGCATGGGCTGGTTCCGCCAGGCTCCAGAGAAGGAGCGTGA
GTTTGTAGCAGCTATTAGCGGGAGTGGACTTGCGACAAGTTATGTAGACTCCGTGAAGGGCCGATTCACCAT
CTCCAGAGACAACGCCAAGAACACGGTGTATCTGCAAATGAACAGCCTGAAACCTGAGGACACGGCCGTTTA
TTACTGTGCCCAGAGATGGACCAGCGGCACTATAGCGAGAGCCACGGGGGAGTATGGCTACTGGGGCCAGG
GGACCCAGGTCACCGTCTCCTCA

0A08

Polypeptide sequence (SEQ ID NO:4):
QVQLVESGGGLVQAGGSLRLSCTDSGRTFSVKPMGWFRQAPGKEREFVAAASFTGVSTFYADSVKDRFTIFRDKD
KNAMDLQINSLKPEDTGAYYCAGTTRTLWGSKWRDVLEYEYWGQGTQVTVSS

Nucleic acid sequence (SEQ ID NO:22):
CAGGCTCAGGTACAGCTGGTGGAGTCTGGGGGAGGATTGGTGCAGGCTGGGGGCTCTCTGAGACTCTCCTG
TACAGACTCTGGACGCACCTTCAGTGTAAAACCCATGGGCTGGTTCCGGCAGGCTCCAGGGAAGGAGCGTGA
GTTTGTAGCAGCTGCAAGTTTTACTGGTGTGAGCACATTCTACGCAGACTCCGTGAAGGACCGATTCACCATC
TTCCGAGACAAGGACAAGAACGCGATGGATCTGCAAATTAACAGCCTGAAACCTGAGGACACGGGCGCGTA
TTACTGTGCAGGAACCACCCGAACATTATGGGGTAGTAAATGGAGAGATGTTCTTGAATACGAATATTGGGG
CCAGGGGACCCAGGTCACCGTCTCCTCA

1B08

Polypeptide sequence (SEQ ID NO:5):
QVQLVESGGGLVQAGGSLRLSCTDSGRTFSVKPMGWFRQAPGMEREFVAAASFTGVSTFYADSVKDRFAIFRDK
DKNTMDLQINSLKPEDTGAYYCAGTTRTLWGSKWRDVLEYEYWGQGTQVTVSS

Nucleic acid sequence (SEQ ID NO:23):
CAGGCTCAGGTACAGCTGGTGGAGTCTGGGGGAGGCTTGGTGCAGGCTGGGGGCTCTCTGAGACTCTCCTG
TACAGACTCTGGACGCACCTTCAGTGTAAAACCCATGGGCTGGTTCCGGCAGGCTCCAGGGATGGAGCGTGA
GTTTGTAGCAGCTGCAAGTTTTACTGGTGTGAGCACATTCTACGCAGACTCCGTGAAGGACCGATTCGCCATC
TTCCGAGACAAGGACAAGAACACGATGGATCTGCAAATTAACAGCCTGAAACCTGAGGACACGGGCGCGTAT
TACTGTGCAGGAACCACCCGAACATTATGGGGTAGTAAATGGAGAGATGTTCTTGAATACGAATATTGGGGC
CAGGGGACCCAGGTCACCGTCTCCTCA

0A07

Polypeptide sequence (SEQ ID NO:6):
QVQLVESGGGLVQAGGSLRLSCTDSGRTFSVKPMGWFRQAPGMEREFVAAASFTGVSTFYADSVKDRFTIFRDK
DKNTMDLQINSLKPEDTGAYYCAGTTRTLWGSKWRDVLEYEYWGQGTQVTVSS

Nucleic acid sequence (SEQ ID NO:24):
CAGGCTCAGGTACAGCTGGTGGAGTCTGGGGGAGGATTGGTGCAGGCTGGGGGCTCTCTGAGACTCTCCTG
TACAGACTCTGGACGCACCTTCAGTGTAAAACCCATGGGCTGGTTCCGGCAGGCTCCAGGGATGGAGCGTGA
GTTTGTAGCAGCTGCAAGTTTTACTGGTGTGAGCACATTCTACGCAGACTCCGTGAAGGACCGATTCACCATC
TTCCGAGACAAGGACAAGAACACGATGGATCTGCAAATTAACAGCCTGAAACCTGAGGACACGGGCGCGTAT
TACTGTGCAGGAACCACCCGAACATTATGGGGTAGTAAATGGAGAGATGTTCTTGAATACGAATATTGGGGC
CAGGGGACCCAGGTCACCGTCTCCTCA

(51) Int. Cl.
*C07K 16/00* (2006.01)
*C12N 7/00* (2006.01)

(52) U.S. Cl.
CPC .... *C07K 2317/569* (2013.01); *C07K 2317/76* (2013.01); *C07K 2317/94* (2013.01)

(56) References Cited

PUBLICATIONS

Muyldermans et al., (Protein Engineering. vol. 7, No. 9; pp. 1129-1135, 1994). (Year: 1994).*

Arbabi-Ghahroudi, M., et al. (2009) Isolation of monoclonal antibody fragments from phage display libraries. Methods Mol Biol. 502:341-64.

Baral, T.N., et al. (2013) Single domain antibodies and their utility. Curr Protoc Immunol. 103:IV:2.17:2.17.1-2.17.57.

Chakchouk-Mtibaa, A., et al. (2014) Characterization of the bacteriocin BacJ1 and its effectiveness for the inactivation of *Salmonella typhimurium* during turkey escalope storage. Food Chem. 152:566-72.

Conrath, K.E., et al. (2003) Emergence and evolution of functional heavy-chain antibodies in Camelidae. Dev Comp Immunol. 27(2):87-103.

Cox, N.A., et al. (2014) Sampling naturally contaminated broiler carcasses for *Salmonella* by three different methods. J Food Prot. 77(3):493-5.

Dougan, G., et al. (1988) Construction and characterization of vaccine strains of *Salmonella* harboring mutations in two different aro genes. J Infect Dis. 158(6): 1329-35.

Doyle, M.P., Erickson, M.C. (2006) Reducing the carriage of foodborne pathogens in livestock and poultry. Poult Sci. 85(6):960-73.

Hagihara, Y. et al. (2007) Stabilization of an immunoglobulin fold domain by an engineered disulfide bond at the buried hydrophobic region. J Biol Chem. 14;282(50):36489-95.

Hugas, M., Beloeil, P., et al. (2014) Controlling *Salmonella* along the food chain in the European Union—progress over the last ten years. Euro Surveill. 19(19).

Hussack, G., et al. (2011) Engineered single domain antibodies with high protease resistance and thermal stability. PLoS One. 6(11):e28218.

Hussack, G., et al. (2014) Protease-resistant single-domain antibodies inhibit *Campylobacter jejuni* motility. Protein Eng Des Sel. 27(6):191-8.

Kalmokoff, M. (2006) Proteomic analysis of *Campylobacter jejuni* 1 1 168 biofilms reveals a role for the motility complex in biofilm formation. J Bacteriol. 188(12) :4312-20.

Lefranc, M.P., et al. (2003) IMGT unique numbering for immunoglobulin and T cell receptor variable domains and Ig superfamily V-like domains. Dev Comp Immunol. 27(1 ):55-77.

Malorny, B., et al. (2004) Diagnostic Real-Time PCR for Detection of *Salmonella* in Food. Appl Environ Microbiol. 70(12): 7046-7052.

Mazengia, E., et al. (2014) Prevalence, concentrations, and antibiotic sensitivities of *Salmonella* serovars in poultry from retail establishments in Seattle, Washington. J Food Prot. 77(6):885-93.

Messens, W., et al. (2013) Estimating the public health impact of setting targets at the European level for the reduction of zoonotic *Salmonella* in certain poultry populations. Int J Environ Res Public Health. 10:4836-50.

Muyldermans, S., et al. (1994) Sequence and structure of VH domain from naturally occurring camel heavy chain immunoglobulins lacking light chains. Protein Eng. 7(9):1 129-1 135.

Muyldermans, S. (2013) Nanobodies: natural single-domain antibodies. Annu Rev Biochem. 82:775-97.

Pace, C.N., et al. (1995) How to measure and predict the molar absorption coefficient of a protein. Protein Sci. (11):241 1-2423.

Popoff, M.Y., and L. Le Minor (1997) Antigenic formulas of the *Salmonella* serovars, 7th revision. W.H.O. Collaborating Centre for Reference and Research on *Salmonella*. Institut Pasteur, Paris, France.

Porwollik, et al. (2004) Characterization of *Salmonella enterica* Subspecies I Genovars by Use of Microarrays. J Bacteriol. 186(17):5883-5898.

Ravel, A., et al. (2010) Seasonality in human salmonellosis: assessment of human activities and chicken contamination as driving factors. Foodborne Pathog Dis. 7(7):785-94.

Rodriguez, A., et al. (2006) Prevalence of *Salmonella* in diverse environmental farm samples. J Food Prot. 69(11):2576-80.

Saerens, D., et al. (2008) Disulfide Bond introduction for general stabilization of immunoglobulin heavy-chain variable domains. J Mol Biol. 377(2):478-88.

Waseh, S., et al. (2010) Orally administered P22 phage tailspike protein reduces *Salmonella* colonization in chickens: prospects of a novel therapy against bacterial infections. PLoS One 5(11):e13904.

International Search Report, dated Apr. 15, 2016 for corresponding International Application No. PCT/IB2016/050546.

Written Opinion of the ISA, dated Apr. 15, 2016 for corresponding International Application No. PCT/IB2016/050546.

Rementeria, A. et al., "Characterization of a Monoclonal Antibody Directed against *Salmonella enterica* Serovar Typhimurium and Serovar [4,5,12:i:_/", Applied and Environmental Microbiology, Mar. 2009 (Mar. 2009), vol. 75, No. 5, pp. 1345-1354 doi: 10.1128/AEM.05197-08.

Hiriart, Y. et al., "Generation and selection of anti-flagellin monoclonal antibodies useful for serotyping *Salmonella enterica*", SpringerPlus 2013, 2:640, doi: 10.1186/2193-1801-2-640.

Nowacka, A., "Isolation of *Salmonella* Serovar-Specific Single Domain Antibodies", A Thesis Presented to the University of Guelph, Ontario, Canada, Sep. 30, 2014 (Sep. 30, 2014).

* cited by examiner

4E08

Polypeptide sequence (SEQ ID NO:1):

HVQLVESGGGLVQAGGSLRLSCAASGLDFSSYAMGWFRQAPGEEREYVAGISRFGGRLYYADSVKGRFTISRDNA
KNTVYLQMNSLKPEDTAIYHCAADRRSGLGTSKEYDYWGQGTQVTVSS

Nucleic acid sequence (SEQ ID NO:19):

CATGTGCAGCTGGTGGAGTCTGGGGGAGGATTGGTGCAGGCTGGGGGCTCTCTGAGACTCTCCTGTGCAGC
CTCTGGACTGGACTTCAGTAGCTATGCCATGGGCTGGTTCCGCCAGGCTCCAGGAGAGGAGCGTGAGTACGT
AGCAGGTATTAGTAGATTTGGTGGTAGGCTCTACTATGCAGACTCCGTGAAGGGCCGATTCACCATCTCCAGA
GACAACGCCAAGAACACGGTGTATCTGCAAATGAACAGTCTGAAACCTGAGGACACGGCCATTTATCACTGT
GCAGCCGATAGACGGTCGGGGTTGGGGACCAGTAAGGAGTATGACTACTGGGGCCAGGGGACCCAGGTCA
CCGTCTCCTCA

1E08

Polypeptide sequence (SEQ ID NO:2):

QVQLVESGGGLVQAGGSLRLSCAASGLDFSSYAMGWFRQAPGEEREYVAGISRFGGRLYYADSVKGRFTISRDNA
KNTVYLQMNSLKPEDTAIYHCAADRRSGLGTSKEYDYWGQGTQVTVSS

Nucleic acid sequence (SEQ ID NO:20):

CAGGCTCAGGTACAGCTGGTGGAGTCTGGGGGAGGATTGGTGCAGGCTGGGGGCTCTCTGAGACTCTCCTG
TGCAGCCTCTGGACTGGACTTCAGTAGCTATGCCATGGGCTGGTTCCGCCAGGCTCCAGGAGAGGAGCGTGA
GTACGTAGCAGGTATTAGTAGATTTGGTGGTAGGCTCTACTATGCAGACTCCGTGAAGGGCCGATTCACCATC
TCCAGAGACAACGCCAAGAACACGGTGTATCTGCAAATGAACAGTCTGAAACCTGAGGACACGGCCATTTAT
CACTGTGCAGCCGATAGACGGTCGGGGTTGGGGACCAGTAAGGAGTATGACTACTGGGGCCAGGGGACCCA
GGTCACCGTCTCCTCA

0A09

Polypeptide sequence (SEQ ID NO:3):

QVQLVESGGGLVQAGGSLRLSCAASGRSFSLYGMGWFRQAPEKEREFVAAISGSGLATSYVDSVKGRFTISRDNA
KNTVYLQMNSLKPEDTAVYYCAQRWTSGTIARATGEYGYWGQGTQVTVSS

Nucleic acid sequence (SEQ ID NO:21):

CAGGCTCAGGTACAGCTGGTGGAGTCTGGGGGAGGATTGGTGCAGGCTGGGGGGTCTCTGAGACTCTCCTG
TGCAGCCTCTGGACGCAGCTTCAGTCTTTATGGCATGGGCTGGTTCCGCCAGGCTCCAGAGAAGGAGCGTGA
GTTTGTAGCAGCTATTAGCGGGAGTGGACTTGCGACAAGTTATGTAGACTCCGTGAAGGGCCGATTCACCAT
CTCCAGAGACAACGCCAAGAACACGGTGTATCTGCAAATGAACAGCCTGAAACCTGAGGACACGGCCGTTTA
TTACTGTGCCCAGAGATGGACCAGCGGCACTATAGCGAGAGCCACGGGGGAGTATGGCTACTGGGGCCAGG
GGACCCAGGTCACCGTCTCCTCA

Polypeptide sequence (SEQ ID NO:4):

QVQLVESGGGLVQAGGSLRLSCTDS<u>GRTFSVKP</u>MGWFRQAPGKEREFVAA<u>ASFTGVST</u>FYADSVKDRFTIFRDKD
KNAMDLQINSLKPEDTGAYYC<u>AGTTRTLWGSKWRDVLEYEY</u>WGQGTQVTVSS

Nucleic acid sequence (SEQ ID NO:22):

CAGGCTCAGGTACAGCTGGTGGAGTCTGGGGGAGGATTGGTGCAGGCTGGGGGCTCTCTGAGACTCTCCTG
TACAGACTCTGGACGCACCTTCAGTGTAAAACCCATGGGCTGGTTCCGGCAGGCTCCAGGGAAGGAGCGTGA
GTTTGTAGCAGCTGCAAGTTTTACTGGTGTGAGCACATTCTACGCAGACTCCGTGAAGGACCGATTCACCATC
TTCCGAGACAAGGACAAGAACGCGATGGATCTGCAAATTAACAGCCTGAAACCTGAGGACACGGGCGCGTA
TTACTGTGCAGGAACCACCCGAACATTATGGGGTAGTAAATGGAGAGATGTTCTTGAATACGAATATTGGGG
CCAGGGGACCCAGGTCACCGTCTCCTCA

<u>1B08</u>

Polypeptide sequence (SEQ ID NO:5):

QVQLVESGGGLVQAGGSLRLSCTDS<u>GRTFSVKP</u>MGWFRQAPGMEREFVAA<u>ASFTGVST</u>FYADSVKDRFAIFRDK
DKNTMDLQINSLKPEDTGAYYC<u>AGTTRTLWGSKWRDVLEYEY</u>WGQGTQVTVSS

Nucleic acid sequence (SEQ ID NO:23):

CAGGCTCAGGTACAGCTGGTGGAGTCTGGGGGAGGCTTGGTGCAGGCTGGGGGCTCTCTGAGACTCTCCTG
TACAGACTCTGGACGCACCTTCAGTGTAAAACCCATGGGCTGGTTCCGGCAGGCTCCAGGGATGGAGCGTGA
GTTTGTAGCAGCTGCAAGTTTTACTGGTGTGAGCACATTCTACGCAGACTCCGTGAAGGACCGATTCGCCATC
TTCCGAGACAAGGACAAGAACACGATGGATCTGCAAATTAACAGCCTGAAACCTGAGGACACGGGCGCGTAT
TACTGTGCAGGAACCACCCGAACATTATGGGGTAGTAAATGGAGAGATGTTCTTGAATACGAATATTGGGGC
CAGGGGACCCAGGTCACCGTCTCCTCA

<u>0A07</u>

Polypeptide sequence (SEQ ID NO:6):

QVQLVESGGGLVQAGGSLRLSCTDS<u>GRTFSVKP</u>MGWFRQAPGMEREFVAA<u>ASFTGVST</u>FYADSVKDRFTIFRDK
DKNTMDLQINSLKPEDTGAYYC<u>AGTTRTLWGSKWRDVLEYEY</u>WGQGTQVTVSS

Nucleic acid sequence (SEQ ID NO:24):

CAGGCTCAGGTACAGCTGGTGGAGTCTGGGGGAGGATTGGTGCAGGCTGGGGGCTCTCTGAGACTCTCCTG
TACAGACTCTGGACGCACCTTCAGTGTAAAACCCATGGGCTGGTTCCGGCAGGCTCCAGGGATGGAGCGTGA
GTTTGTAGCAGCTGCAAGTTTTACTGGTGTGAGCACATTCTACGCAGACTCCGTGAAGGACCGATTCACCATC
TTCCGAGACAAGGACAAGAACACGATGGATCTGCAAATTAACAGCCTGAAACCTGAGGACACGGGCGCGTAT
TACTGTGCAGGAACCACCCGAACATTATGGGGTAGTAAATGGAGAGATGTTCTTGAATACGAATATTGGGGC
CAGGGGACCCAGGTCACCGTCTCCTCA

Polypeptide sequence (SEQ ID NO:7):

QVQLVESGGGLVQAGGSLSLSCEDSGRSFSVKPMAWFRQAPGLEREFVAAASFTGVSTFYADSVKDRYTIFREKD
NNTVYLQMNSLQPEDTGAYYCAGTLRTLWGSKWRDRREYEYWGQGTQVTVSS

Nucleic acid sequence (SEQ ID NO:25):

CAGGCTCAGGTACAGCTGGTGGAGTCTGGGGGGGGATTGGTGCAGGCTGGGGGCTCTCTGAGTCTCTCCTG
CGAAGACTCTGGACGCTCCTTCAGTGTAAAGCCCATGGCCTGGTTCCGGCAGGCTCCAGGGCTGGAGCGTGA
GTTTGTAGCAGCTGCAAGTTTCACTGGTGTGAGCACATTCTATGCAGACTCCGTGAAGGACCGATACACCATC
TTCAGAGAGAAGGACAATAACACGGTGTATCTGCAAATGAACAGCCTACAACCTGAGGACACGGGCGCGTAT
TATTGTGCAGGAACCCTCCGAACGCTATGGGGTAGTAAATGGCGGGATCGTCGTGAATACGAATATTGGGGC
CAGGGGACCCAGGTCACCGTCTCCTCA

2A09

Polypeptide sequence (SEQ ID NO:8):

QVQLVESGGGLVQPGGSLRLSCAASGIIFSINAMGWYRQAPGKQRELVARISAYDHTNYADSVKGRFTISRDNAK
NTVYLQMNSLKPEDTAVYYCNVDEIRKFWGQGTQVTVSS

Nucleic acid sequence (SEQ ID NO:26):

CAGGCTCAGGTACAGCTGGTGGAGTCTGGGGGAGGCTTGGTGCAGCCTGGGGGGTCTCTGAGACTCTCCTG
TGCAGCCTCTGGAATTATCTTCAGTATCAATGCCATGGGGTGGTATCGCCAGGCTCCAGGGAAGCAGCGCGA
GTTGGTCGCACGTATTAGTGCTTATGATCATACAAACTATGCAGACTCCGTGAAGGGCCGATTCACCATCTCC
AGAGACAACGCCAAGAACACGGTGTATCTGCAAATGAACAGCCTGAAACCTGAGGACACGGCCGTCTATTAC
TGTAATGTAGATGAAATACGGAAATTCTGGGGCCAGGGGACCCAGGTCACCGTCTCCTCA

0H12

Polypeptide sequence (SEQ ID NO:9):

QVQLVESGGGLVQPGGSLRLSCTDSGRTFSVKPMGWFRQAPGMEREFVAAASFTGVSTFYADSVKDRFTIFRDK
DKNTMDLQINSLKPEDTGAYYCAGTTRTLWGSKWRDVLEYEYWGQGTQVTVSS

Nucleic acid sequence (SEQ ID NO:27):

CAGGCTCAGGTACAGCTGGTGGAGTCTGGGGGAGGCTTGGTGCAGCCTGGGGGGTCTCTGAGACTCTCCTG
TACAGACTCTGGACGCACCTTCAGTGTAAAACCCATGGGCTGGTTCCGGCAGGCTCCAGGGATGGAGCGTGA
GTTTGTAGCAGCTGCAAGTTTTACTGGTGTGAGCACATTCTACGCAGACTCCGTGAAGGACCGATTCACCATC
TTCCGAGACAAGGACAAGAACACGATGGATCTGCAAATTAACAGCCTGAAACCTGAGGACACGGGCGCGTAT
TACTGTGCAGGAACCACCCGAACATTATGGGGTAGTAAATGGAGAGATGTTCTTGAATACGAATATTGGGGC
CAGGGGACCCAGGTCACCGTCTCCTCA

Polypeptide sequence (SEQ ID NO:10):

QVKLEESGGGLVQAGGSLRLSCAASGLDFSSYAMGWFRQAPGEEREYVAGISRFGGRLYYADSVKGRFTISRDNA
KNTVYLQMNSLKPEDTAIYHCAADRRSGLGTSKEYDYWGQGTQVTVSS

Nucleic acid sequence (SEQ ID NO:28):

CAGGTAAAGCTGGAGGAGTCTGGGGGAGGATTGGTGCAGGCTGGGGGCTCTCTGAGACTCTCCTGTGCAGC
CTCTGGACTGGACTTCAGTAGCTATGCCATGGGCTGGTTCCGCCAGGCTCCAGGAGAGGAGCGTGAGTACGT
AGCAGGTATTAGTAGATTTGGTGGTAGGCTCTACTATGCAGACTCCGTGAAGGGCCGATTCACCATCTCCAGA
GACAACGCCAAGAACACGGTGTATCTGCAAATGAACAGTCTGAAACCTGAGGACACGGCCATTTATCACTGT
GCAGCCGATAGACGGTCGGGGTTGGGGACCAGTAAGGAGTATGACTACTGGGGCCAGGGGACCCAGGTCA
CCGTCTCCTCA

1H07

Polypeptide sequence (SEQ ID NO:11):

QVKLEESGGGLVQAGGSLRLSCTDSGRTFSKKPMGWFRQAPGMEREFVAAASYTGVSTFYADSVKDRFTIFRDKD
KNTMDLQINSLKPEDTGAYYCAGTTRTLWGSKWRDVLEYEYWGQGTQVTVSS

Nucleic acid sequence (SEQ ID NO:29):

CAGGTAAAGCTGGAGGAGTCTGGGGGAGGATTGGTGCAGGCTGGGGGCTCTCTGAGACTCTCCTGTACAGA
CTCTGGACGCACCTTCAGTAAAAAACCCATGGGCTGGTTCCGGCAGGCTCCAGGGATGGAGCGTGAGTTTGT
AGCAGCTGCAAGTTATACTGGTGTGAGCACATTCTATGCAGACTCCGTGAAGGACCGATTCACCATCTTCAGA
GACAAGGACAAGAACACGATGGATCTGCAAATTAACAGCCTGAAACCTGAGGACACGGGCGCGTATTATTGT
GCAGGAACCACCCGAACATTATGGGGTAGTAAATGGCGAGATGTCCTTGAATACGAATATTGGGGCCAGGG
GACCCAGGTCACCGTCTCCTCA

1E03

Polypeptide sequence (SEQ ID NO:12):

QVKLEESGGGLVQAGGSLSLSCEDSGRSFSVKPMAWFRQAPGLEREFVAAASFTGVSTFYADSVKDRYTIFREKDN
NTVYLQMNSLQPEDTGAYYCAGTLRTLWGSKWRDRREYEYWGQGTQVTVSS

Nucleic acid sequence (SEQ ID NO:30):

CAGGTAAAGCTGGAGGAGTCTGGGGGAGGATTGGTGCAGGCTGGGGGCTCTCTGAGTCTCTCCTGCGAAGA
CTCTGGACGCTCCTTCAGTGTAAAGCCCATGGCCTGGTTCCGGCAGGCTCCAGGGCTGGAGCGTGAGTTTGT
AGCAGCTGCAAGTTTCACTGGTGTGAGCACATTCTATGCAGACTCCGTGAAGGACCGATACACCATCTTCAGA
GAGAAGGACAATAACACGGTGTATCTGCAAATGAACAGCCTACAACCTGAGGACACGGGCGCGTATTATTGT
GCAGGAACCCTCCGAACGCTATGGGGTAGTAAATGGCGGGATCGTCGTGAATACGAATATTGGGGCCAGGG
GACCCAGGTCACCGTCTCCTCA

Polypeptide sequence (SEQ ID NO:13):

QVKLEESGGGLVQPGGSLRLSCAASGIIFSINAMGWYRQAPGKQRELVARISAYDHTNYADSVKGRFTISRDNAKN
TVYLQMNSLKPEDTAVYYCNVDEIRKFWGQGTQVTVSS

Nucleic acid sequence (SEQ ID NO:31):

CAGGTAAAGCTGGAGGAGTCTGGGGGAGGCTTGGTGCAGCCTGGGGGGTCTCTGAGACTCTCCTGTGCAGC
CTCTGGAATTATCTTCAGTATCAATGCCATGGGGTGGTATCGCCAGGCTCCAGGGAAGCAGCGCGAGTTGGT
CGCACGTATTAGTGCTTATGATCATACAAACTATGCAGACTCCGTGAAGGGCCGATTCACCATCTCCAGAGAC
AACGCCAAGAACACGGTGTATCTGCAAATGAACAGCCTGAAACCTGAGGACACGGCCGTCTATTACTGTAAT
GTAGATGAAATACGGAAATTCTGGGGCCAGGGGACCCAGGTCACCGTCTCCTCA

1A07

Polypeptide sequence (SEQ ID NO:14):

QVKLEESGGGLVQPGGSLRLSCTDSGRTFSVKPMGWFRQAPGMEREFVAAASFTGVSTFYADSVKDRFTIFRDKD
KNTMDLQINSLKPEDTGAYYCAGTTRTLWGSKWRDVLEYEYWGQGTQVTVSS

Nucleic acid sequence (SEQ ID NO:32):

CAGGTAAAGCTGGAGGAGTCTGGGGGAGGCTTGGTGCAGCCTGGGGGGTCTCTGAGACTCTCCTGTACAGA
CTCTGGACGCACCTTCAGTGTAAAACCCATGGGCTGGTTCCGGCAGGCTCCAGGGATGGAGCGTGAGTTTGT
AGCAGCTGCAAGTTTTACTGGTGTGAGCACATTCTACGCAGACTCCGTGAAGGACCGATTCACCATCTTCCGA
GACAAGGACAAGAACACGATGGATCTGCAAATTAACAGCCTGAAACCTGAGGACACGGGCGCGTATTACTGT
GCAGGAACCACCCGAACATTATGGGGTAGTAAATGGAGAGATGTTCTTGAATACGAATATTGGGGCCAGGG
GACCCAGGTCACCGTCTCCTCA

4C10

Polypeptide sequence (SEQ ID NO:15):

QVKLEESGGGSVQAGGSLRLSCAVSGSIFSGDAMGWYRQAPGKKREYVALIGKEGDTVYADSVKGRFTISRDNAK
NTFYLQMNNLEPEDTARYICATFEERPQPSYVYWGPGTQVTVSS

Nucleic acid sequence (SEQ ID NO:33):

CAGGTAAAGCTGGAGGAGTCTGGGGGAGGCTCGGTGCAGGCTGGGGGGTCTCTGAGACTCTCCTGTGCAGT
CTCTGGAAGCATCTTCAGTGGTGATGCCATGGGCTGGTACCGCCAGGCTCCAGGAAAGAAGCGCGAGTATGT
CGCGTTAATTGGTAAGGAAGGTGACACAGTCTACGCAGACTCTGTGAAGGGCCGCTTCACCATCTCCAGAGA
CAATGCCAAGAACACGTTCTATCTACAAATGAACAACCTGGAACCTGAGGACACGGCCAGATATATTTGTGCG
ACATTCGAGGAGCGACCCCAACCATCGTATGTCTACTGGGGCCCGGGGACCCAGGTCACCGTCTCCTCA

Polypeptide sequence (SEQ ID NO:16):

QVKLVDSGGGLVQAGGSLRLSCTDSGRTFSKKPMGWFRQAPGMEREFVAAASYTGVSTFYADSVKDRFTIFRDK
DKNTMDLQINSLKPEDTGAYYCAGTTRTLWGSKWRDVLEYEYWGQGTQVTVSS

Nucleic acid sequence (SEQ ID NO:34):

CAGGTAAAGCTGGTGGATTCTGGGGGAGGATTGGTGCAGGCTGGGGGCTCTCTGAGACTCTCCTGTACAGA
CTCTGGACGCACCTTCAGTAAAAAACCCATGGGCTGGTTCCGGCAGGCTCCAGGGATGGAGCGTGAGTTTGT
AGCAGCTGCAAGTTATACTGGTGTGAGCACATTCTATGCAGACTCCGTGAAGGACCGATTCACCATCTTCAGA
GACAAGGACAAGAACACGATGGATCTGCAAATTAACAGCCTGAAACCTGAGGACACGGGCGCGTATTATTGT
GCAGGAACCACCCGAACATTATGGGGTAGTAAATGGCGAGATGTCCTTGAATACGAATATTGGGGCCAGGG
GACCCAGGTCACCGTCTCCTCA

4F12

Polypeptide sequence (SEQ ID NO:17):

QVQLVESGGGLVQAGGSLRLSCAASGLDFSSYAMGWFRQAPGEEREYVAGISRFGGRLYYADSVKGRFTISRDNA
KNTVYLQMNSLKPEDTAIYHCAADRRSGLGTSKEYDYWGQGTQVTVSS

Nucleic acid sequence (SEQ ID NO:35):

CAGGTGCAGCTGGTGGAGTCTGGGGGAGGATTGGTGCAGGCTGGGGGCTCTCTGAGACTCTCCTGTGCAGC
CTCTGGACTGGACTTCAGTAGCTATGCCATGGGCTGGTTCCGCCAGGCTCCAGGAGAGGAGCGTGAGTACGT
AGCAGGTATTAGTAGATTTGGTGGTAGGCTCTACTATGCAGACTCCGTGAAGGGCCGATTCACCATCTCCAGA
GACAACGCCAAGAACACGGTGTATCTGCAAATGAACAGTCTGAAACCTGAGGACACGGCCATTTATCACTGT
GCAGCCGATAGACGGTCGGGGTTGGGGACCAGTAAGGAGTATGACTACTGGGGCCAGGGGACCCAGGTCA
CCGTCTCCTCA

0D12

Polypeptide sequence (SEQ ID NO:18):

QVQLVESGGGLVQAGGSLRLSCTDSGRTFSKKPMGWFRQAPGMEREFVAAASYTGVSTFYADSVKDRFTISRDK
DKNTMDLQINSLKPEDTGAYYCAGTTRTLWGSKWRDVLEYEYWGQGTQVTVSS

Nucleic acid sequence (SEQ ID NO:36):

CAGGTGCAGCTGGTGGAGTCTGGGGGAGGATTGGTGCAGGCTGGGGGCTCTCTGAGACTCTCCTGTACAGA
CTCTGGACGCACCTTCAGTAAAAAACCCATGGGCTGGTTCCGGCAGGCTCCAGGGATGGAGCGTGAGTTTGT
AGCAGCTGCAAGTTATACTGGTGTGAGCACATTCTATGCAGACTCCGTGAAGGACCGATTCACCATCTCCAGA
GACAAGGACAAGAACACGATGGATCTGCAAATTAACAGCCTGAAACCTGAGGACACGGGCGCGTATTATTGT
GCAGGAACCACCCGAACATTATGGGGTAGTAAATGGCGAGATGTCCTTGAATACGAATATTGGGGCCAGGG
GACCCAGGTCACCGTCTCCTCA

FIG. 1F

ANTI-SALMONELLA ANTIBODIES AND USES THEREOF

CROSS-REFERENCE TO RELATED APPLICATIONS

This application is a U.S. National Phase application, under 35 U.S.C. § 371, of International Application no. PCT/IB2016/050546, with an international filing date of Feb. 3, 2016, and claims benefit of U.S. Application No. 62/112,035 filed on Feb. 4, 2015, and which are hereby incorporated by reference for all purposes.

FIELD OF THE INVENTION

The field of the present invention relates generally to antibodies, fragments thereof, derivatives thereof, and to uses and applications of such antibodies. The antibodies and fragments described may be specifically directed against *Salmonella.*

BACKGROUND ART

*Salmonellosis* is one of the most commonly reported zoonotic diseases in humans. In the United States alone, it causes an estimated 1.3 million human food-borne illnesses and more than 500 deaths each year (Messens et al., 2013). *Salmonella* serotypes *enteritidis* and *typhimurium* are frequently detected in human infections (Ravel et al., 2010). Salmonellas are widely distributed in nature, and they are commonly carried by wild or farm-animal vectors. Poultry is known to be a major global reservoir of Salmonellas. *Salmonella* live in poultry gut as transient members of the intestinal microbial population without causing disease. Colonization of *Salmonella* does not usually affect poultry body weight gain or performance; thus, asymptomatic infection can increase the likelihood of zoonotic transmission to humans through the food chain (Hugas et al., 2014; Mazengia et al., 2014). Chicks can become infected vertically (from adults via the egg to the chick) or horizontally (from the environment, pests, or feed) (Cox et al., 2014; Rodriguez et al., 2006).

*Salmonella enterica* is one of the two main *Salmonella* species that causes gastroenteritis in humans. *S. enterica* is subdivided into 6 subspecies and almost all human infections are caused by subspecies I (*enterica*). More than 2600 serovars of *S. enterica* have been identified (Popoff and Le Minor, 1997); however, only a few of these serovars are responsible for most *Salmonella* infections in human and domestic animals (Porwollik et al., 2004).

The large and growing market for broiler chickens and eggs, and the emergence of antibiotic resistant strains of *Salmonella* have led to public health concerns, change in government regulation policies in Europe and North America and further demands to enact laws to control *Salmonella* levels in poultry (Hugas, et al., 2014).

Vaccination strategies in broiler chickens have shown sub-optimal results to-date mostly due to the short life span of the birds. Currently, two types of *Salmonella* vaccines are commercially available; an attenuated live vaccine and an inactivated vaccine. These vaccines are often administered to both breeder and layer flocks, but their effectiveness depends on the targeted serovar, host species, and whether reduction rather than eradication is the objective (Doyle and Erickson, 2006). These vaccines do not eliminate initial colonization of the mucosal surfaces, particularly in the young bird (Dougan et al., 1988). Effective control depends upon a number of factors, including improved on-farm biosecurity, use of best practices in husbandry and use of vaccination and competitive exclusion products and feed additives. Preventive hygienic measures typically involve establishing effective farm-site biosecurity and poultry house sanitation protocols. Other more targeted strategies are being developed. For instance, a combination of *Salmonella*-specific lytic phages has been recently approved in Europe for applications in food packaging. Others have proposed and tested inclusion of bacteriocins and/or tail-spike phage protein (Chakchouk-Mtibaa et al., 2014; Waseh et al., 2010) in the poultry feed for controlling *Salmonella* but to date none of these products has been commercialized.

It would be advantageous to provide antibodies or fragments thereof that assist in the reduction, prevention and/or treatment of *Salmonella* infection.

SUMMARY OF THE INVENTION

This disclosure refers to the development of camelid single domain antibodies (VHHs) that bind to *Salmonella*. VHHs are the smallest antigen binding fragments that can be readily expressed in bacteria or yeast in large quantities and at a significantly lower cost compared to conventional antibodies.

Accordingly, disclosed herein is an isolated antibody or antibody fragment comprising an amino acid sequence of any one of SEQ ID NOS:1-18, or a variant thereof. In one embodiment, the isolated antibody or antibody fragment binds directly to the exterior of *Salmonella*, optionally to *Salmonella* flagella.

In a preferred embodiment of the present disclosure, the *Salmonella*-binding antibody or antibody fragment comprises a CDR1 comprising an amino acid sequence of $GRX_1FSX_2KP$; a CDR2 comprising an amino acid sequence of $ASX_3TGVST$; and a CDR3 comprising an amino acid sequence of $AGTX_4RTLWGSKWRDX_5X_6EYEY$; wherein $X_1$ is T or S; $X_2$ is V or K; $X_3$ is F or Y; $X_4$ is T or L; $X_5$ is V or R; and $X_6$ is L or R.

In another preferred embodiment, the *Salmonella*-binding antibody or antibody fragment comprises a CDR1 comprising an amino acid sequence of GLDFSSYA; a CDR2 comprising an amino acid sequence of ISRFGGRL; and a CDR3 comprising an amino acid sequence of AADRRSGLGTSKEYDY.

In another preferred embodiment, the *Salmonella*-binding antibody or antibody fragment comprises a CDR1 comprising an amino acid sequence of GIIFSINA; a CDR2 comprising an amino acid sequence of ISAYDHT; and a CDR3 comprising an amino acid sequence of NVDEIRKF.

In another preferred embodiment, the *Salmonella*-binding antibody or antibody fragment comprises a CDR1 comprising an amino acid sequence of GRSFSLYG; a CDR2 comprising an amino acid sequence of ISGSGLATS; and a CDR3 comprising an amino acid sequence of AQRWTSGTIARATGEYGY.

In another preferred embodiment, the *Salmonella*-binding antibody or antibody fragment comprises a CDR1 comprising an amino acid sequence of GSIFSGDA; a CDR2 comprising an amino acid sequence of IGKEGDT; and a CDR3 comprising an amino acid sequence of ATFEERPQPSYVY.

In a preferred embodiment of the present disclosure, the isolated antibody or antibody fragment disclosed herein is modified for tolerance to one or more gut enzymes selected from the group consisting of pepsin, trypsin and chymotrypsin. In a further preferred embodiment, the antibody or antibody fragment disclosed herein comprises a detectable label.

The present disclosure further provides a nucleic acid molecule encoding the isolated antibody or antibody fragment disclosed herein, a host cell comprising the nucleic acid molecule, and a bacteriophage comprising the nucleic acid or the polypeptide.

Another preferred aspect of the present disclosure is a method of reducing the presence of *Salmonella* in an animal or an animal environment comprising administering to the animal the isolated antibody or antibody fragment disclosed herein. In one preferred embodiment, the method further comprises administering an antibiotic, bacteriocin, or other plant- or animal-derived compound effective against *Salmonella* to the animal. In another preferred embodiment, the method further comprises administering a competing microbe to the animal together with an antibody or antibody fragment disclosed herein, optionally co-expressed or co-contained in a probiotic system. The antibody or antibody fragment may be administered orally; the animal may be a chicken, optionally a laying hen or broiler chicken; and the animal environment may be a poultry farm.

Also disclosed is a method of reducing or preventing introduction of *Salmonella* into an animal environment comprising administering to an inductee animal the antibody or antibody fragment disclosed herein, prior to introducing the inductee animal into the animal environment.

Also disclosed is a method of treating a *Salmonella* infected subject comprising administering to the subject the isolated antibody or antibody fragment disclosed herein. In a preferred embodiment, the method of treating an infected subject further comprises administering to the subject antibiotic effective against *Salmonella*. The subject may be a livestock animal selected from the group consisting of a chicken, cow, or sheep, or the subject may be a human.

Also disclosed is a formulation for use in treating *Salmonella* infection comprising the isolated antibody or antibody fragment disclosed herein and a pharmaceutically acceptable excipient.

Further disclosed is a use of the isolated antibody or antibody fragment disclosed herein for treating *Salmonella* infection in a subject in need thereof.

Further disclosed is a method of detecting *Salmonella* in a sample comprising contacting the sample with the isolated antibody or antibody fragment disclosed herein, and detecting the presence of bound antibody or antibody fragment. In one preferred embodiment, the sample comprises a bodily fluid or fecal material. In another preferred embodiment, the sample comprises a food product or a surface swab from a food product.

Another aspect of the present disclosure is a kit for conducting the detection method, comprising the isolated antibody or antibody fragment disclosed herein and instructions for use in detecting *Salmonella*.

Another aspect provides use of the antibody or antibody fragment disclosed herein for preparation of a medicament for treatment of *Salmonella* infection.

BRIEF DESCRIPTION OF THE DRAWINGS

Further aspects and advantages will become apparent from the following description taken together with the accompanying drawings in which:

FIG. 1 shows exemplary amino acid sequences of the anti-*Salmonella* antibodies and antibody fragments of the present disclosure and nucleic acid sequences encoding said antibodies and antibody fragments;

DETAILED DESCRIPTION

Figure 2:
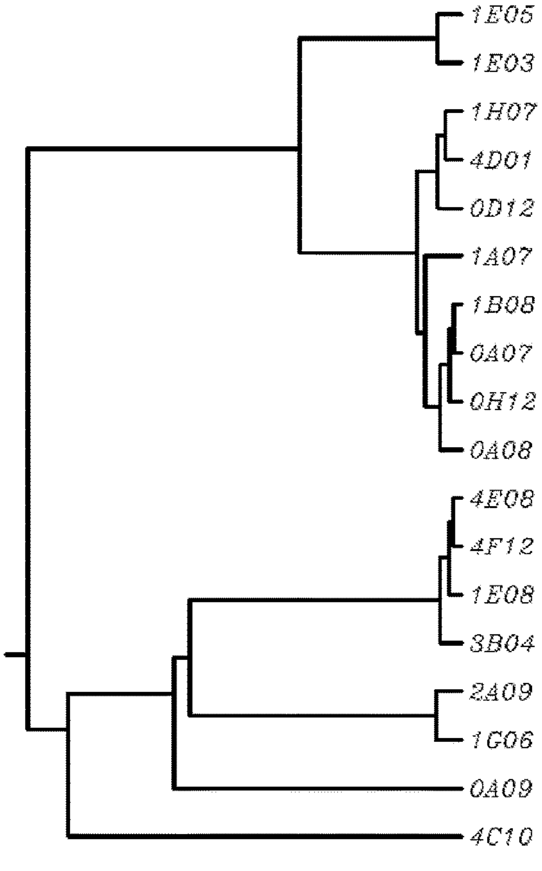
FIG. 2 is a dendrogram showing amino acid sequence similarities between the anti-*Salmonella* antibodies and antibody fragments.

The present disclosure is based on the creation, isolation, and characterization of antibodies and antibody fragments that preferably have the ability to bind to the exterior of *Salmonella* cells. Features and uses of said antibodies and antibody fragments will now be described in greater detail. It will be appreciated that exemplary embodiments presented herein are within the scope of the present invention and are not intended as limiting. Reference is made to the Figures which relate to preferred embodiments of the present invention.

Definitions

The term "antibody" as used herein refers to a full length immunoglobulin that has the ability to bind to an antigen. The term "antibody fragment" as used herein refers to a less than full length portion of an immunoglobulin molecule—for example, a VHH domain—which retains the ability to bind to an antigen.

The term "VHH" or "VHH domain" as used herein refers to a single domain antibody derived from a heavy chain antibody raised in a camelid animal, such as a llama, alpaca, or camel. Other terms for VHHs sometimes used in the art include but are not limited to: single domain antibodies (sdAbs), single variable domain antibodies, immunoglobulin single variable domains, heavy-chain variable domain antibodies, and Nanobodies™.

The term "isolated" or "purified" as used herein in association with a polypeptide, antibody, antibody fragment or a nucleic acid means a polypeptide, antibody, antibody fragment or nucleic acid that is substantially or essentially free of naturally associated molecules—for example, an isolated antibody that is substantially or essentially free of antibodies having different specificities.

The term "multimeric" or "multivalent" as used herein refers to having multiple antigen-binding locations on a polypeptide, typically from multiple copies of an antibody or antibody fragment, or from a plurality of similar but different such antibodies or antibody fragments.

The term "nucleic acid" as used herein refers to double stranded or single stranded DNA, RNA molecules or DNA/RNA hybrids. These molecules may be nicked or intact as found in living cells. The double stranded or single stranded nucleic acid molecules may be linear or circular. The duplexes may be blunt ended or have single stranded tails, for example, with sticky ends created by restriction endonucleases.

The term "variant" as used herein refers to an amino acid or nucleotide sequence having at least 80% identity or sequence homology with a subject amino acid or nucleotide sequence.

Antibodies and Antibody Fragments

According to one aspect of the present disclosure, provided herein is an isolated antibody or antibody fragment comprising an amino acid sequence of any one of SEQ ID NOS:1-18, or a variant thereof. In a preferred embodiment, said antibody or antibody fragment binds to *Salmonella*. In a further preferred embodiment, said antibody or antibody fragment binds to the flagella of *Salmonella*. The aforementioned antibodies or antibody fragments are preferably derived from a collection of antibodies raised in alpacas that were immunized with heat inactivated *Salmonella* cells, as described in these Examples below. Each of SEQ ID NOS: 1-18 corresponds to the amino acid sequence of an isolated VHH domain from said collection and said sequences are shown in FIGS. 1A, 1B, 1C, 1D, 1E and 1F.

VHH domains are comprised of framework regions interspersed with three complementarity determining regions (CDRs): CDR1, CDR2, and CDR3. CDR sequences are known to be essential for the specificity of binding between antibodies (or antibody fragments) and antigens. Accordingly, in a preferred embodiment of the present disclosure, the antibody or antibody fragment disclosed herein comprises a CDR1 comprising an amino acid sequence of GLDFSSYA (SEQ ID NO:40); a CDR2 comprising an amino acid sequence of ISRFGGRL (SEQ ID NO:41); and a CDR3 comprising an amino acid sequence of AADRRSGLGTSKEYDY (SEQ ID NO:42). In another preferred embodiment, CDR1 comprises an amino acid sequence of GIIFSINA (SEQ ID NO:43); CDR2 comprises an amino acid sequence of ISAYDHT (SEQ ID NO:44); and CDR3 comprises an amino acid sequence of NVDEIRKF (SEQ ID NO:45). In another preferred embodiment, CDR1 comprises an amino acid sequence of GRSFSLYG (SEQ ID NO:46); CDR2 comprises an amino acid sequence of ISGSGLATS (SEQ ID NO:47); and CDR3 comprises an amino acid sequence of AQRWTSGTIARATGEYGY (SEQ ID NO:48). In a further preferred embodiment, CDR1 comprises an amino acid sequence of GSIFSGDA (SEQ ID NO:49); CDR2 comprises an amino acid sequence of IGKEGDT (SEQ ID NO:50); and CDR3 comprises an amino acid sequence of ATFEERPQPSYVY (SEQ ID NO:51).

Consensus sequences can be defined based on some of the above-specified CDR sequences, as described in the Examples below and illustrated in Table 2. In a preferred embodiment of the present disclosure, an isolated antibody or antibody fragment is herein provided that binds *Salmonella* and comprises a CDR1 comprising an amino acid sequence of $GRX_1FSX_2KP$ (SEQ ID NO:37); a CDR2 comprising an amino acid sequence of $ASX_3TGVST$ (SEQ ID NO:38); and a CDR3 comprising an amino acid sequence of $AGTX_4RTLWGSKWRDX_5X_6EYEY$ (SEQ ID NO:39); wherein $X_1$ is T or S; $X_2$ is V or K; $X_3$ is F or Y; $X_4$ is T or L; $X_5$ is V or R; and $X_6$ is L or R. Optionally, CDR1 comprises an amino acid sequence of GRTFSVKP (SEQ ID NO:52); CDR2 comprises an amino acid sequence of ASFTGVST (SEQ ID NO:53); and CDR3 comprises an amino acid sequence of AGTTRTLWGSKWRDVLEYEY (SEQ ID NO:54). Optionally, CDR1 comprises an amino acid sequence of GRSFSVKP (SEQ ID NO:55); CDR2 comprises an amino acid sequence of ASFTGVST (SEQ ID NO:53); and CDR3 comprises an amino acid sequence of AGTLRTLWGSKWRDRREYEY (SEQ ID NO:56). Optionally, CDR1 comprises an amino acid sequence of GRTFSKKP (SEQ ID NO:57); CDR2 comprises an amino acid sequence of ASYTGVST (SEQ ID NO:58); and CDR3 comprises an amino acid sequence of AGTTRTLWGSKWRDVLEYEY (SEQ ID NO:54).

Any of the antibody fragments described herein may be utilized in an isolated form, or may form a portion of a longer molecule, such as within an antibody, for example a recombinant antibody, a chimeric antibody, a small molecule conjugated antibody, a human antibody, or a humanized antibody.

Furthermore, an antibody fragment may include, but is not limited to Fv, single-chain Fv (scFv; a molecule consisting of $V_L$ and $V_H$ connected with a peptide linker), Fab, Fab', and $F(ab')_2$, or single domain antibody (sdAb). SdAbs may be of camelid origin, and thus may be based on camelid framework regions; alternatively, the CDRs may be grafted onto the framework regions of other antibody domains, for example but not limited to VNAR, human $V_H$ or human $V_L$ framework regions.

The present invention includes modifications of the antibodies or antibody fragments disclosed herein, and may include amino acid variations, including conservative substitutions, additions or deletions, provided at least 80%, preferably at least 90%, identity or sequence homology is observed and provided such a modification results in a functional variant. In a preferred embodiment, the percent identity is set at 90% or greater, and thus it is to be understood that an identity of each VHH domain can, for example, be individually determined as 90%, 91%, 92%, 93%, 94%, 95%, 96%, 97%, 98% or 99% of specified sequences.

It will be appreciated that the present antibodies or antibody fragments can also be preferably produced in multimeric forms. For example, a dimer or pentamer can be formed. Antibody fragments, such as VHHs, that are used to form a multimer may be the same or different from each other. Pentavalent multimeric VHH domains, or pentabodies, may possess higher affinity binding to an antigen as compared with monovalent VHH domains. The five VHH domains need not be identical to one another, and as such may comprise VHH domains of different sequences.

The antibodies or antibody fragments described herein may preferably be modified for tolerance or resistance to one or more gut enzymes. Typical gut enzymes which may have a destructive effect on a polypeptide include pepsin, trypsin and chymotrypsin. Thus, resistance to these enzymes is advantageous, as the peptide would have more exposure time to bind with ambient *Salmonella* within the intestinal tract. Single domain antibodies are, in general, significantly more resistant to proteases than conventional antibodies.

Furthermore, VHHs are known to be amenable to polypeptide engineering for optimization of biophysical features including heat and protease resistance (Hussack et al., 2014). Scaffold engineering of portions of the polypeptide both inside and outside of the CDR regions are known in the art and can confer increased target affinity, protease resistance, as well as thermal and low pH resistance. For example, to favour the entropy of binding, the extended flexible CDR3 loop may be constrained with an interloop disulfide bond that connects CDR1 and CDR3, or CDR2 position 55 and CDR3 or FR2 at position 50 and CDR3 (Muyldermans, 2013; Conrath et al, 2003). The cysteine of CDR3 that participates in either disulfide bond formation mentioned above can occur or be placed at any position of the extended CDR3 loop (Conrath et al, 2003). The stability of a VHH can be increased by introducing cysteine at position 54 and 78 to form an additional disulfide bond. This disulfide bond is known to make VHHs highly resistant to degradation by pepsin or chymotrypsin (Hagihara et al, 2007; Saerens et al, 2008; Hussack et al, 2014).

The antibodies or antibody fragments described herein may preferably be labeled with an acceptable label and optionally a linker as needed. The label may be rendered detectable or may in itself be detectable, so that the presence of binding to *Salmonella* can be observed. The antibody or antibody fragment may be linked to a radioisotope, a paramagnetic label such as gadolinium or iron oxide, a fluorophore, Near Infra-Red (NIR) fluorochrome or dye, an echogenic microbubble, an affinity label (for example biotin, avidin, etc), enzymes, or any other suitable agent that may be detected by diagnostic imaging methods.

The antibodies or antibody fragments described herein may be produced in any of the ways known in the art. For example, antibodies or antibody fragments may be expressed in a cell containing an encoding expression vector. Such expression systems are well known in the art and many variations may be used. Examples of cell-based expression systems may be *Saccharomyces cerevisiae, Bacillus subtilis, Bacillus brevis, Bacillus megaterium, Lactobacillus* species, *Escherichia coli, Pichia pastoris, Aspergillus niger*, and mammalian-derived cell lines such as CHO, HEK, or HeLa cells. The expressed antibody or antibody fragment can be isolated from a solution of lysed cells or the polypeptide may be secreted into media and isolated directly therefrom. The antibody or antibody fragment may also be artificially synthesized. Examples of artificial protein synthesis include solid-phase peptide synthesis, liquid-phase peptide synthesis, and cell-free protein synthesis, also known as in vitro protein synthesis.

Nucleic Acids, Cells, and Bacteriophages

Nucleic acid molecules encoding the amino acid sequences described above are encompassed herein. In one embodiment, the nucleic acid molecule comprises a nucleic acid sequence of any one of SEQ ID NOS:19-36. These sequences are illustrated in FIGS. 1A, 1B, 1C, 1D, 1E and 1F. Given the degeneracy of the genetic code, a number of variant nucleic acid sequences would have the effect of encoding the amino acid, as would be readily understood by one skilled in the art. The nucleic acid molecules of the present invention may be double stranded or single stranded DNA, RNA molecules or DNA/RNA hybrids. These molecules may be nicked or intact as found in living cells. The double stranded or single stranded nucleic acid molecules may be linear or circular. The duplexes may be blunt ended or have single stranded tails, for example, with sticky ends created by restriction endonucleases.

A host cell comprising the nucleic acid molecule encoding any one of the antibody or antibody fragment described herein would also be readily recognized by the skilled artisan. The host cell could be a bacterium, such as a desired strain of *E. coli*, a yeast cell, such as a desired strain of *Pichia pastoris*, a mammalian-derived cell line such as CHO, HEK, or HeLa cells, or any other host cell suitable for carrying the nucleic acid molecule of the present invention.

A bacteriophage comprising the antibody or antibody fragment described herein, and/or comprising the nucleotide molecule encoding the antibody or antibody fragment is also encompassed in the present invention.

Methods, Uses, Formulations, and Kits

The antibodies or antibody fragments described herein can specifically bind to *Salmonella* and it will be appreciated that said antibodies or antibody fragments may be useful for a number of purposes, including reducing *Salmonella*, inhibiting *Salmonella* and/or detecting *Salmonella* in a subject.

Accordingly, provided herein are methods of reducing the presence of *Salmonella* in an animal or an animal environment comprising administering to the animal an antibody or antibody fragment disclosed herein.

Within an individual animal, reducing the presence of *Salmonella* may comprise reducing contamination on the surface of the animal, or within the gastrointestinal tract of an animal. Should an animal be systemically infected, the method described herein could be used for reducing the presence of *Salmonella*.

The environment of an animal can preferably relate to the animal's immediate surroundings, such as the walls or floors of a cage or facility, the feeding or watering apparatuses within an animal compound, the bedding materials found in an animal compound, or simply the fecal material present external to the animal within the animal's confines.

Administering to an animal the antibody or antibody fragment described herein can preferably be for the purpose of reducing or inhibiting the presence of *Salmonella* within the animal to which the antibody or antibody fragment is administered, or an offspring of such an animal, or within the flock, cage or barn in which the animal lives. Reducing *Salmonella* within the animal's gastrointestinal tract is one way to reduce contamination within the animal's environment, leading to a safer food supply chain with lower incidence of contamination.

Co-administration of another substance that is effective against *Salmonella* is also a possible strategy for reducing *Salmonella* in an animal environment. For example, administering to the animal an antibiotic either at the same time as a co-formulation or at an adjacent time to the delivery of the antibody or antibody fragment can have an additive effect or may have a synergistic effect. The result of which may be a reduced likelihood of *Salmonella* contamination, but also reduced usage of antibiotic (i.e., fractional usage of antibiotic with synergistic efficacy). A bacteriocin effective against *Salmonella* can also be provided to the animal with the antibody or antibody fragment for an additive or synergistic effect. In addition to, or as an alternative to bacteriocin, any other plant- or animal-derived compound, such as a small molecule, peptide, or protein, that has an effect against *Salmonella* may be used together with the antibody or antibody fragment described herein. A competitive microbe may also be provided to the animal concurrently with the antibody or antibody fragment in order to possibly achieve an additive or a synergistic effect. The competitive microbe may be used together with the antibody or antibody fragment described herein as part of a probiotic system. Within such a probiotic system, the antibody or antibody fragment may be co-administered with the competitive microbe, or may be delivered sequentially. Expression of the antibody or antibody fragment within a probiotic system of the polypeptide described herein may also be undertaken.

The antibody or antibody fragment described herein may be administered orally to a subject. Oral delivery permits the polypeptide to be delivered within the water or food supply to an animal, and is less noticeable or stressful to an animal than an injection. Gavage is also an acceptable oral route when highly accurate delivery of an oral dosing regime is desirable. Other routes of administration can also be considered, such as inhalation, intranasal, gel-based or by spray, in ovo, topically or by injection such as intravenous, subcutaneous, intramuscular, intraorbital, intraocular, intradermal, gel-based, spray or rectal delivery route. The antibody or antibody fragment may be administered directly or within a phage or host microorganism.

As described above, modifications to the antibody or antibody fragment described herein may be made to increase efficacy of oral delivery. For example, scaffold engineering can be performed on portions of the antibody or antibody fragment within or outside of the CDR regions to confer protease resistance, as well as thermal and low pH resistance. However, and in addition, the form of antibody or antibody fragment delivery may also be altered with pharmaceutically acceptable coatings or excipients that provide a protective effect against gut enzymes, thermal or low pH effects. In this way, the sequence of the antibody or antibody fragment itself need not be modified, but rather the formulation prepared for oral delivery may itself be more optimal for the species of subject to which the antibody or antibody fragment is to be delivered. The antibody or antibody fragment may also be conjugated to small molecules such as cyclic peptides, macromolecules or polyethylene glycol to improve delivery or stability.

The dosage form may be of any type acceptable for antibody or antibody fragment delivery to animals. Coated forms and slow release forms could be used if desirable. Liquid, powder, crystal, gel, semi-solid, or tablet forms can be used.

The animal to which the antibody or antibody fragment may be delivered may preferably be a bird, such as a broiler chicken or laying hen. Other types of livestock animals, such as swine, cows, sheep, etc. may also benefit from the peptide if *Salmonella* is present in the animal's gut or surrounding environment. A preferred animal environment may be a barn or farm, such as a poultry farm.

In order to avoid contamination of an animal environment that is substantially free of *Salmonella*, a method is provided that aims to prevent introduction of a new contaminated animal or "inductee" animal into the environment, such as a barn. In such a method, the antibody or antibody fragment is administered to an inductee prior to introducing the inductee animal into the animal environment, such as a barn or farm. In this way, the animal could be cleared for the likelihood of contamination prior to taking up residence with the other animals who may have already received treatment.

The antibody or antibody fragment may also be administered to plants or plant-based materials by spraying or by other methods to reduce a level of contaminating *Salmonella*. Examples of such plants or plant-based materials include but are not limited to salads and spices.

Also disclosed is a method of treating a *Salmonella* infected subject comprising administering to the subject an antibody or antibody fragment disclosed herein. In a preferred embodiment, the method further comprises administering to the subject antibiotic effective against *Salmonella*.

The subject may be a livestock animal selected from the group consisting of a chicken, cow, or sheep, or the subject may be a human.

Also disclosed is a formulation for use in treating *Salmonella* infection comprising an antibody or antibody fragment disclosed herein and an excipient.

Also disclosed is a use of an antibody or antibody fragment disclosed herein for treating *Salmonella* infection in a subject in need thereof.

Also disclosed is a method of detecting *Salmonella* in a sample comprising contacting the sample with an antibody or antibody fragment disclosed herein, and detecting the presence of bound antibody or antibody fragment. In one preferred embodiment, the sample comprises a bodily fluid or fecal material. In another preferred embodiment, the sample comprises a food product or a surface swab from a food product.

For detection purposes, samples from a subject may comprise a bodily fluid or fecal material. The subject may be a human or a non-human animal. Samples of microbiota can be collected from the gastrointestinal (GI) tract or gut of a subject. Methods of sample collection are known to those skilled in the art. For example, microbiota samples may be obtained from stools, intestinal mucosal biopsies, gut lavage or combinations thereof. Collection can be performed during endoscopy by flushing a physiological solution, such as sterile saline solution or sterile water, onto the mucosa to remove the strongly adherent mucus layer overlying mucosal epithelial cells and the microbial community embedded within the mucus layer. Aspirates are then collected directly through an endoscope at a specific location in the gut and the samples are placed on ice.

Collection of gut microbiota can also be performed on stools. Collection of bacteria from stools is known in the art. In the case of fecal microbiota collection and analysis, fresh stools may be collected, immediately processed, and the processed materials can be stored at about −80° C.

For detection purposes, the subject may be a chicken, optionally a broiler chicken. Samples from such a subject may comprise intestinal fluid, carcass, feathers, skin, breast/leg meat rinses, as well as droppings from poultry or a bodily fluid, or rectal effluent. Samples may be taken from the environment such as the floor covering of barns, boots, wash/chill tanks or any other equipment used at a poultry processing facility as well as animal feed and water.

Once a sample has been collected, the presence of bound antibody or antibody fragment in said sample can be detected by carrying out any one of a number of binding assays or bound substrate detection procedures known in the art. Antibody or antibody fragment binding can be measured directly or indirectly by using a tagged version of the antibody or antibody fragment, examples of which are described above. The step of detecting may be accomplished by any suitable method known in the art, for example, but not limited to: optical imaging, immunohistochemistry or molecular diagnostic imaging, ELISA, or other suitable method.

Also disclosed is a kit for conducting the detection method, comprising an antibody or antibody fragment disclosed herein and instructions for use in detecting *Salmonella*.

Exemplary embodiments of the present disclosure will now be described. These embodiments involve preparation and use of camelid single-domain antibodies (VHHs) specific for *Salmonella*, and are not intended as limiting.

EXAMPLES

Example 1

Immunization of Alpaca with Different Strains of *Salmonella*

To isolate VHH domains that target *Salmonella*, three alpacas were immunized with different strains of *Salmonella enterica*.

Three male alpacas (*Vicugna pacos*) were immunized subcutaneously with *Salmonella enterica* serovars. Five injections were performed in total. Each animal was injected with a mixture of 4 *Salmonella eneterica* strains ($1\times10^9$ cfu from each) that were heat inactivated (30 min at 65° C.) and mixed with adjuvant (aluminum hydroxide, Alhydrogel™ 2%). The injection groups consisted of:

1—*S. Typhimurium* (SGSV1412, and SGSC4904), *S. Entritidis* (SGSC4901, SGSC3820);

2—*S. Newport* (SGSC4910), *S. Javiana* (SGSC4917), *S. Senftenberg* (SGSC2516), *S. Heidelberg* (SGSC4966); and 3—*S. Hadar* (SGSC4906), *S. Kentucky* (SGSC4914), *S. Infantis* (SGSC4905), *S. SaintPaul* (SGSC4920).

To prepare antigens for injection, *Salmonella* were cultured on LB agar plates. Approximately $1\times10^9$ cells were treated with heat at 65° C. for 30 minutes in order to completely kill the bacteria. For each injection, a total of $4\times10^9$ killed cells were used with equal mixture of 4 different strains in a total volume of 0.4 ml. The contents were mixed with an equal volume of Alhydrogel™ (Sigma™). Injections were done at days 1, 15, 22, 29, and 36. Alpaca serum was analyzed for specific binding to a commercially available purified flagellin from *S. Typhimurium* or the whole bacteria cells immobilized on the plates. Briefly, microtiter plates (Maxisorp™ plates) (Nalge Nunc International™, Rochester, N.Y.) were coated overnight at 4° C. with 5 μg/ml of flagellin antigen in PBS. Wells were rinsed and blocked with 200 μl of 5 mg/ml Bovine Serum Albumin or 1% casein. Different dilutions of serum were added and incubated at room temperature for 1.5 h. Wells were washed with PBST (0.05% v/v Tween-20™), and incubated with goat anti-llama IgG (H+L) (1:1,000 in PBS) (Bethyl Laboratories™, Montgomery, Tex.) followed by Rabbit-anti-goat-HRP (1:5,000 in PBS) (Bethyl Laboratories™, Montgomery, Tex.). Signal was detected by adding 100 μl/well TMB peroxidase substrate (Kirkegaard and Perry Laboratories™, Gaithersburg, Md., USA). Reactions were stopped by adding 100 1M phosphoric acid and A450 was measured using a Bio-Rad™ ELISA plate reader.

Example 2

Phage Display Library Constructions

A hyper-immunized alpaca VHH library was constructed based on RNA isolated from the lymphocytes of animals immunized as in Example 1.

A phage display library was constructed using a standard protocol (Arbabi Ghahroudi et al., 2009). Lymphocytes were collected from the blood using Lymphoprep™ Tubes (Axis-Shield™, Oslo, Norway). Total RNA was isolated from approximately $1\times10^7$ lymphocytes collected on day 36 post-immunization using RNAzol™ kit (Bioshop™, Burlington, Ontario, Canada). First-strand cDNA was synthesized with oligo(dT) primers from the SuperScript III First Strand™ cDNA synthesis kit (Invitrogen™, Burlington, Ontario, Canada) using 6 μg total RNA as template according to manufacturer's recommendations. Variable and part of the constant domains DNA were amplified using oligonucleotides MJ1-3 (sense) and two CH2 domain antisense primers, CH2 and CH2b3 (for primer sequences see Arbabi Ghahroudi et al., 2009; Baral et al. 2013) and heavy chain fragments (550-650 bp in length) were purified using the E.Z.N.A.™ Cycle Pure PCR purification Kit (Omega Bio-tek™ Norcross, Ga., USA). The variable regions of heavy chain antibodies (IgG2 and IgG3) were re-amplified in a second PCR reaction using MJ7 and LP6-MJ8 primers (for primer sequences, see Baral et al. 2013). The amplified PCR products were purified with the Cycle Pure Kit™ (Omega Bio-tek™), digested with SfiI (Thermoscientific™, Toronto, Ontario, Canada), and re-purified using the same kit. Twelve micrograms of digested VHH fragments were ligated with 40 μg (1:3 molar ratio, respectively) Sfi-digested pADL-23c phagemid vector (Antibody Design Labs™, San Diego, Calif., USA) using T4 DNA ligase system and its protocol (Promega™, Madison, Wis., USA), transformed into commercial electrocompetent TG1 *E. coli* cells (Lucigen™ Corporation, Middleton, Wis., USA), as described previously (Arbabi Ghahroudi et al., 2009), and a library size of $7.8\times10^8$ transformants was obtained. The VHH fragments from 50 colonies were PCR-amplified and sequenced to analyze the complexity of the library; all clones had inserts of expected sizes and were different from each other at their CDR regions as determined by sequencing of their encoding VHH fragments. The library was grown for 3-4 hours at 37° C., 250 rpm in 2×YT/Carb-Glucose (1% w/v) medium. The bacterial cells were pelleted, resuspended in the same medium and stored as glycerol stock at −80° C. as described previously (Arbabi Ghahroudi et al., 2009).

Example 3

Screening Phage Display Library to Select for VHHs Binding to *Salmonella*

The library screening (panning) was done through a sequential strategy using either whole, heat inactivated *Salmonella* bacteria or purified *Salmonella* flagellin protein (main component of flagella encoded by fliC gene) as a target. For the panning against whole *Salmonella*, the bacterial cells from 4 different strains were equally mixed and adjusted to an OD of 1 using PBS solution. The bacterial mixes were inactivated at 65° C. for 30 minutes and coated on a 96 well Maxisorb™ plate. To pan against flagellin protein (Flagellin from *Salmonella typhimurium*, purchased from Sigma™, cat#: SRP8029), flagellin solution (5 ug/ml, dissolved in PBS solution) was coated on a 96 well Maxisorp™ plate. For each panning, BSA-PBS solution (0.5% of BSA dissolved in PBS solution) was also coated on the same 96-well Maxisorp™ plate as a pre-screening control. The coated plates were then incubated at 4° C. overnight. Next day, the coated wells were rinsed with PBS once and blocked with BSA-PBS solution for 2 h at 37° C. The *Salmonella* phage library was diluted using BSA-PBS solution so that approximately $2\times10^{12}$ phage particles were added first to the BSA-PBS wells and kept at 37° C. for 1 hour and then the supernatant was transferred to the *Salmonella* whole cell or flagellin wells. The phage particles were incubated in the *Salmonella* whole cell or flagellin wells for 2 hours at 37° C. and then washed 5 times with PBST containing 0.1% v/v Tween-20. The bound phages were eluted with 0.1 M triethylamine, neutralized with 1M Tris-HCL, PH 7.4 and incubated with exponentially growing TG1 cells in 10 ml of 2YT medium. After 30 min incubation at 37° C., the cells were superinfected with $10^{11}$ M13KO7 helper phage (New England Biolabs™) for an additional 30 min. Two antibiotics, ampicillin (100 μg/L) and Kanamycin (25 μg/L), were added to the TG1 culture medium. Incubation continued at 37° C. for 16 hours, followed by selection of the phage infected TG1 cells. In the third day of panning, the amplified phage particles in culture supernatant were precipitated with polyethylene glycol (PEG) as described previously (Arbabi-Ghahroudi et al., 2009). Briefly, 10 ml of phage infected TG1 culture was centrifuged at 4000 rpm at 4° C. for 30 minutes, the supernatant was filtered with a 0.22 μm filter and mixed with ⅕ volume of PEG/NaCl (20% PEG, 2.5 M NaCl) on ice for 1 hour. The phages were pelleted by centrifugation at 4000 rpm at 4° C. for 30 minutes. Finally, the enriched phage pool was suspended in 200 μl of PBS and ready for the next round of panning. Panning was continued for three more rounds following the same conditions except that washing was increased 7, 10 and 12 times with PBST for the second, third and fourth rounds of panning, respectively. After four rounds of panning, 96 randomly picked colonies were grown and subjected to phage ELISA screening.

Example 4

Expression and Purification of Monomeric VHH

VHH against flagellin or whole *Salmonella* cells identified in Example 3 were PCR amplified from the pADL23 phagemid vector with BbsI1-VHH forward primer (5'-TATGAAGACACCAGGCCCAGGTAAAGCTGGAGGAGTCT-3') (SEQ ID NO:59) and BamHI-VHH reverse primer (5'-TTGTTCGGATCCTGAGGAGACGGTGACCTG-3') (SEQ ID NO:60). The PCR fragments were digested with the BbsI and BamHI restriction enzymes and ligated into the similarly digested pSJF2 expression vector (Arbabi-Ghahroudi et al., 2009). Upon ligation, all plasmids were transformed into electrocompetent *E. coli* (TG1 strain) and selected on LB agar plates containing carbenicillin. Colonies were screened by colony PCR for inserts and the DNA was sequenced. The sequences were aligned and categorized into 18 different groupings or classes; each represented by one or more clones and each representing the same amino acid sequence (Table 1). A single clone was randomly selected from each class. Nucleic acid and amino acid sequences of the 18 selected VHHs are shown in FIG. 1. CDR1, CDR2, and CDR3 are underlined within each polypeptide sequence. As shown in Table 2, the 18 VHH sequences can be placed in 5 distinct groups based on sequence similarities in the CDR regions.

The VHHs all have the canonical amino acid residues found in Camelid family VHHs at positions 42 (F/Y), 49 (E/Q/A), 50 (R), and 52 (F/V/G/L) (Muyldermans, et al. 1994) according to the IMGT numbering scheme (Lefranc, et al. 2003). In addition, the CDR3 domains in these VHHs are generally larger than CDR3 domains in human VH proteins. For example, the CDR3 domain of Group 1 VHHs is 20 residues in size (Table 2).

Analysis using the full polypeptide sequences of the 18 VHHs reveals that these VHHs can be classified into 2 larger groupings (FIG. 2). The first grouping includes 1E05, 1E03, 1H07, 4D01, 0D12, 1A07, 1B08, 0A07, 0H12 and 0A08; the second grouping includes 4E08, 4F12, 1E08, 3B04, 2A09, 1G06, 0A09 and 4C10.

VHH antibodies were expressed using the standard periplasmic expression method (Arbabi-Ghahroudi et al., 2009). VHH antibody 1E03 was expressed in *P. pastoris* because no expression was achieved using the *E. coli* expression method. After induction of protein expression, cell cultures were harvested at 6,000 rpm×30 min (4° C.), the supernatant decanted, and the periplasmic contents extracted from the cell pellet. Briefly, the pellet of monomeric VHH was resuspended in 20 ml of ice cold TES (0.2 M Tris-HCl pH 8.0, 20% (w/v) sucrose, 0.5 mM EDTA) and incubated on ice for 30 min. Next, 30 ml of ice-cold ⅛ TES (diluted in $dH_2O$) was added, incubated an additional 30 min on ice, and the slurry centrifuged at 9,000 rpm for 30 min (4° C.). The resulting supernatant containing VHH was dialysed overnight against PBS and purified using Profinity™ IMAC resin from BioRad™, as per manufacturer's instructions, with phosphate-based elution buffer containing 500 mM imidazole.

Figure 3:
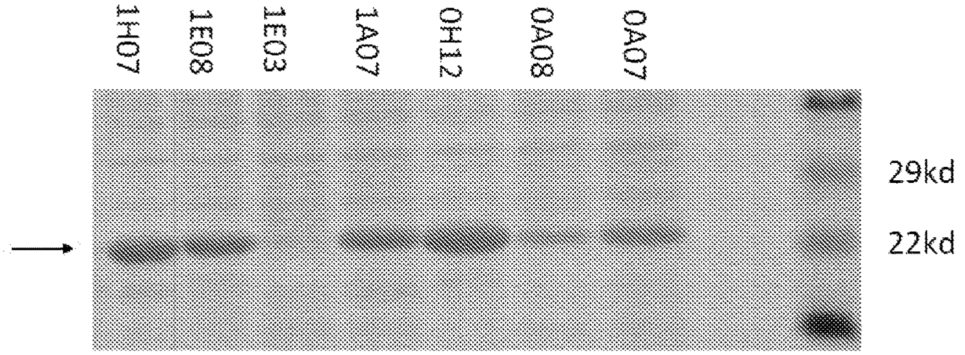
FIG. 3 shows purified anti-*Salmonella* VHH domains on SDS-PAGE gel stained with Coomassie Brilliant Blue™ G250.

Purified protein fractions were pooled and dialyzed against PBS. Eluted fractions were analyzed by SDS-PAGE and Western blotting before being dialysed into PBS. FIG. 3 shows an example of VHH polypeptides on an SDS-PAGE gel stained with Coomassie™ Brilliant Blue G250. The arrow points to the position of the polypeptides. Size of the polypeptides is about 24 kD. Expected size is around 15 kD. The discrepancy is caused by three tags (c-myc, AviTag™ and $His_6$) linked to the VHHs.

VHH concentrations were determined by absorbance measurements at 280 nm using theoretical MW and extinction coefficients calculated with the ExPASy ProtParam™ Tool (expasy.org/tools/protparam.html) according to Pace et al., 1995. The yield of the purified monomeric VHHs ranged from 1 to 20 mg/L bacterial culture.

Example 5

VHH Binding Assays

Figure 4:
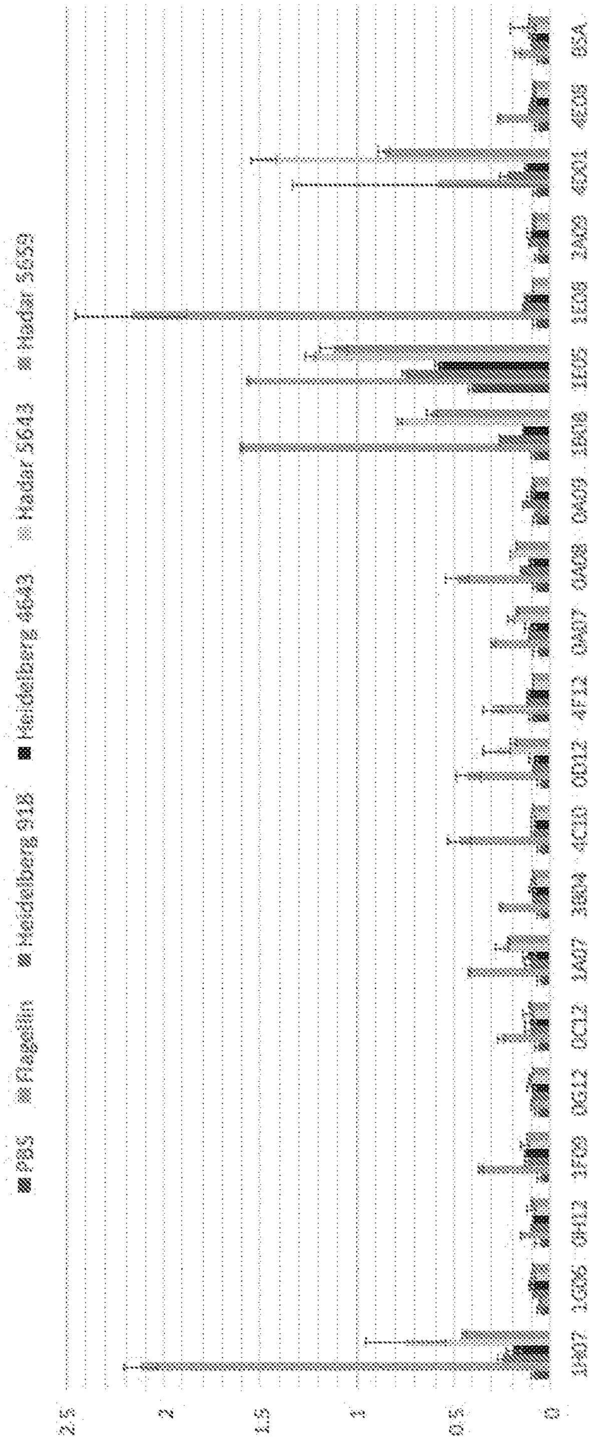
FIG. 4 is a bar graph showing results of a binding assay for 18 different anti-*Salmonella* VHH domains to flagellin of *Salmonella* or whole cells of *Salmonella enterica* strains: S. Heidelberg 918, S. Heidelberg 4643, S. Hadar 5643, or S. Hadar 5659 (binding measured at A450)

Microtitre plates (Maxisorp™ plates) (Nalge Nunc International™, Rochester, N.Y.) were coated overnight at 4° C. with 2.5 μg/mL flagellin (Sigma-Aldrich™ SRP8029) and 14 different heat inactivated (65° C., 30 min) *Salmonella enterica* serovar whole cells. Binding of flagellin and 4 of the *S. enterica* strains is described in Example 1. Wells were rinsed with PBS pH 7.4 and blocked with 200 ul of BSA-PBS solution for 1 hr. Twenty different VHH-containing phages were prepared as described in Example 1 and used to test their binding ability to flagellin or 14 different *Salmonella* strains. Phages in 2YT medium supernatant (100 μL) were added to blocked coated microtitre plates and incubated at room temperature for 1 hour. Wells were washed with PBST solution and incubated with HRP conjugated anti-M13 monoclonal antibody (1:5000 in PBST) (Sigma-Aldrich™ GE27-9421-01) at room temperature for half an hour. Wells were washed again and signal was detected using 50 ul/well TMB peroxidase substrate (Kirkegaard and Perry Laboratories™, Gaithersburg, Md., USA). Reactions were stopped by adding 50 ul/well of 1M hydrochloric acid and A450 was measured using a Cytation™ 5 (Biotek™) multimode reader. As shown in FIG. 4, a number of the VHHs were determined to bind to one or more of *Salmonella* flagellin and/or the *Salmonella* serovar whole cells. For example, robust binding was observed for VHH 1E05 against all inactivated S. Hadar and *S. Heidelberg* strains tested. This assay provides only a qualitative or semi-quantitative assessment of the target binding of the VHHs. Furthermore, binding cannot be discounted for VHHs that were not show to bind according to this assay, as said assay is limited by the presentation of antigen on coated plates and by the variation in growth rates of phages displaying particular VHHs.

Example 6

*Salmonella* Motility Assays

Figure 5:
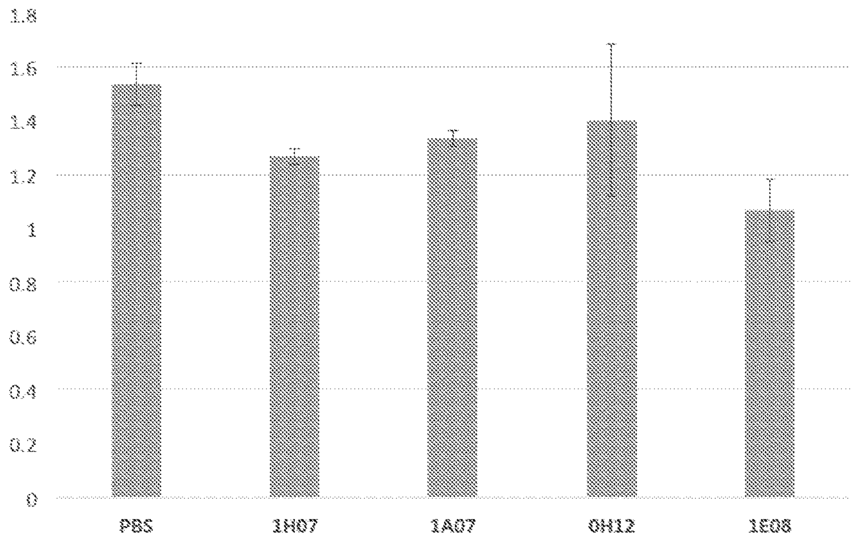
FIG. 5 is a bar graph showing the results of a motility assay for *S. enterica* strain SG4904 in the presence of 4 different anti-*Salmonella* VHH domains (y-axis shows the diameter of the outgrowth of bacterial colonies)

Motility assays was performed as described previously (Kalmokoff et al., 2006). VHHs at a final concentration of 2 μg/μl were plated with *Salmonella* strain 4904 ($1\times10^7$) on Muller-Hinton™ media with 0.35% agar and incubated at 37° C. under microaerophilic conditions (5% $O_2$, 10% $CO_2$ and 85% $N_2$) for 18 hours. Bacterial motility was determined by measuring the diameter of the circle produced by the growing bacteria on the plate. Results are shown in FIG. 5. It was found that VHH 1E08 significantly inhibited bacterial motility.

Example 7

Cell Proliferation Assays

Figure 6:
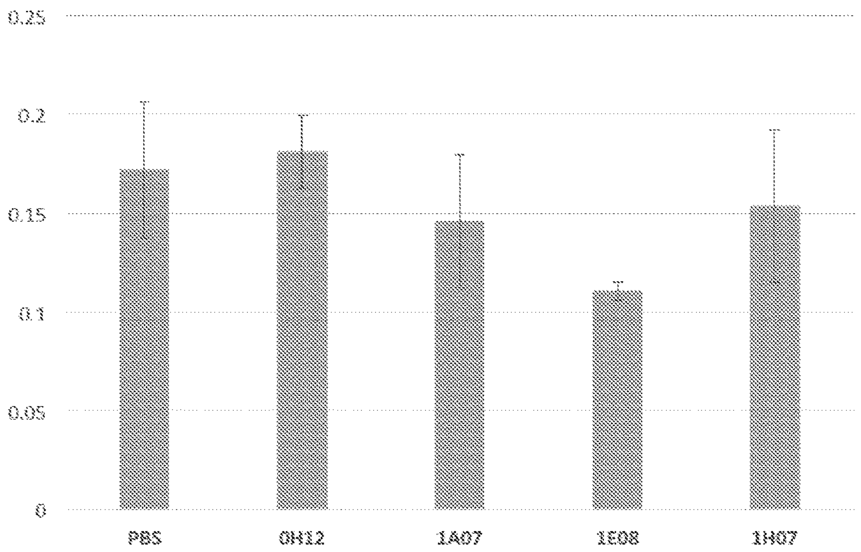
FIG. 6 is a bar graph showing the results of a cell proliferation assay of *S. enterica* strain SG4904 in the presence of 4 different anti-*Salmonella* VHH domains (bacterial growth rate determined by measuring $OD_{600}$)

Around $1\times10^7$ *Salmonella* (strain name: 4904) cells were incubated in 100 μl Muller-Hinton™ liquid medium with 0.2 μg/μl VHHs in a 96 well plate and incubated at 37° C. under microaerophilic conditions (5% $O_2$, 10% $CO_2$ and 85% $N_2$) for 18 hours. Bacterial growth rate was determined by measuring optical density at 600 nm wavelength (FIG. 6). Similar to the motility assay result, VHH 1E08 was found to significantly inhibit the growth of *Salmonella* cells.

Example 8

*Salmonella* Internalization Assays in HeLa Cells

Aim:

to identify anti-*Salmonella* VHH domains that interfere with *Salmonella* colonization of epithelial cells. To colonize the gut, *Salmonella* must attach to the surface and enter the host epithelial cells, where it undergoes intracellular replication. Without wishing to be limited by theory, VHHs that interfere with this process are expected to prevent bacterial attachment and/or allow attachment but block the invasion of the host cell.

Summary of the Assay:

HeLa epithelial cells are challenged with GFP expressing *Salmonella* in the absence or presence of different VHHs. *Salmonella* is allowed to attach and enter the cells and subsequently unbound bacteria are removed. Attached but non-internalized *Salmonella* are eliminated by gentamicin, an antibiotic that does not penetrate epithelial cells. Intracellular growth of *Salmonella* is then tracked by using a fluorescence plate reader, which quantifies the increase of GFP fluorescence over time.

Method:

HeLa cells were grown in 24-well plates containing 500 μl/well of DMEM+10% FBS and incubated at 37° C. in the presence of 5% $CO_2$ for 24 h (80-100% confluence). *Salmonella enterica* serovar Hadar 5643 transformed with GFP was grown on the same day (from an overnight culture) to an OD of approximately 0.5. The culture was centrifuged (5 min, 5000 rpm) and resuspended in DMEM without FBS, and the bacteria were pre-incubated with the VHHs at different concentration for 30 min at 37° C. with gentle mixing. Prior to infection, cells were washed 3× with PBS. *Salmonella* and VHHs were added to the HeLa cells (MOI: 100 in 500 ul/well of DMEM without FBS). The plates were incubated for 1 h at 37° C. in 5% $CO_2$. After 1 h of infection (BEFORE GENTA samples—FIG. 7) cells were washed 3× with PBS to remove non-adherent bacteria. To permeabilize and lyse HeLa cells, 1 ml of 1% saponin was added. The plates were incubated for 15 min at 37° C. in 5% $CO_2$. Bacteria were resuspended by pipetting up and down vigorously (approx. 10 times per well). Serial dilutions were plated on LB agar plates. The plates were incubated overnight at 37° C. to quantify viable intracellular bacteria. DMEM with 10% FBS+gentamicin (100 μg/ml, final conc.) was added to the rest of the plate. After 1 h of infection (AFTER GENTA samples-FIG. 7) cells were washed 3× with PBS to remove non-adherent bacteria. To permeabilize and lyse HeLa cells, 1 ml of 1% saponin was added. The plates were incubated for 15 min at 37° C. in 5% $CO_2$. Bacteria were resuspended by pipetting up and down vigorously (approx 10 times per well). Serial dilutions were plated on LB agar plates. The plates were incubated overnight at 37° C. to quantify viable intracellular bacteria. DMEM with 10% FBS+gentamicin (10 ug/ml, final conc.) was added to the rest of the plates and they were incubated for 24 h at 37° C. in 5% $CO_2$. All assays were performed in duplicate.

Figure 7:
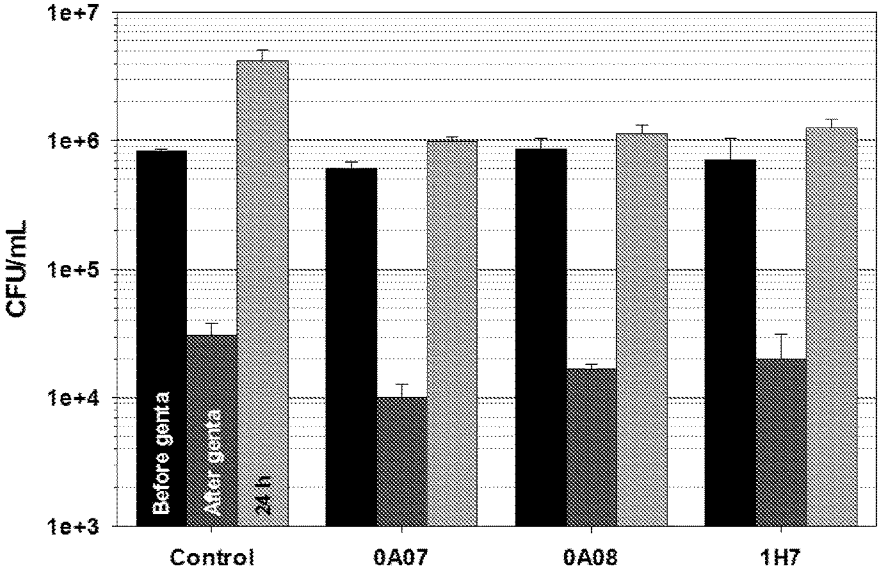
FIG. 7 is a bar graph showing the activity of three VHHs against *S. enterica* serovar Hadar 5643 in a HeLa cell *Salmonella* internalization assay.

Results:

Based on both colony counts and fluorescence quantification of GFP expression, VHH 0A07 showed the highest inhibition of intracellular *S. enterica* strain Hadar 5643 growth (FIG. 7).

Example 9

*Salmonella* Internalization Assays in Chicken Ileum and Jejunum Cultures

Aim:

to identify anti-*Salmonella* VHHs that interfere with *Salmonella* colonization of adult chicken intestine. To colonize the chick gut, *Salmonella* must attach to the surface and enter the host epithelial cells, where it undergoes intracellular replication. Without wishing to be limited by theory, VHHs that interfere with this process are expected to prevent bacterial attachment and/or allow attachment but block the invasion of the host cell.

Method:

Intestinal *jejuni* and ilea were obtained from ten (2×5) 30-day old non-SPF chickens. The *jejuni* and ilea were washed and cut into 0.5×0.8 cm pieces. VHHs 0A07, 0A08, 1E03, 1 H07 and 0H12 were pre-bound to *S. enterica* serovar Hadar 5643 for 30 min. The mixture was applied onto the intestinal sections and the bacteria were allowed to infect for 3 hours. Treatment with gentamicin removed extracellular bacteria. Genomic DNA was extracted from the infected sections and an established robust 5' nuclease (TaqMan™) real-time PCR assay was used to detect *Salmonella* as previously described (Malorny et al., 2004).

Figure 8:
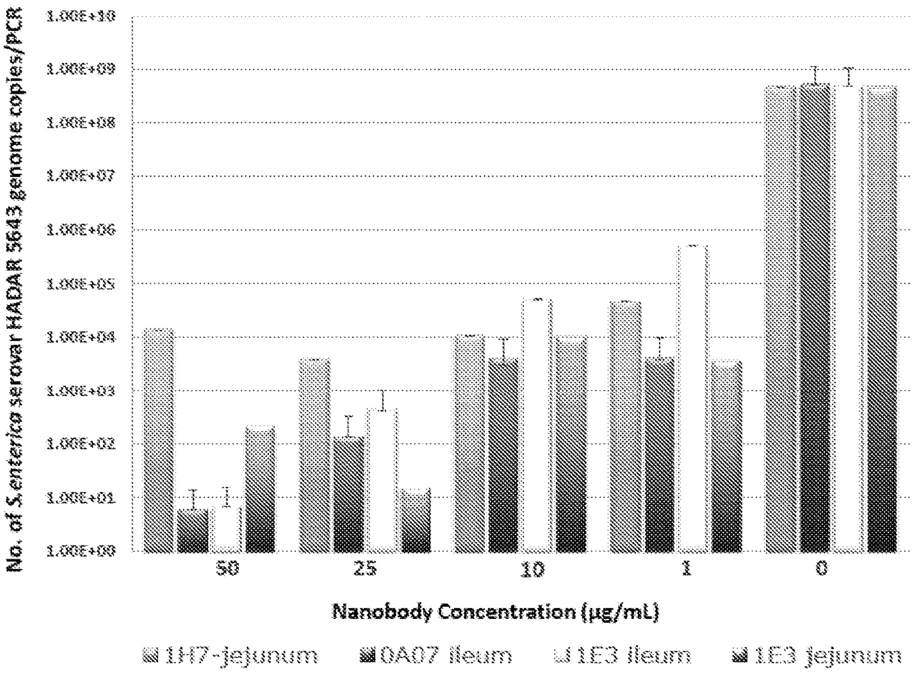
FIG. 8 is a bar graph showing the activity of different concentrations of three VHHs against *S. enterica* serovar Hadar 5643 in a cultured chicken ileum or jejunum *Salmonella* internalization assay, as measured by *Salmonella* genome copy number (based on amplification of the single copy housekeeping gene ttr)

Results:

7.5-log reduction in genome copy number was achieved with the 0A07, 1E03 VHH treatment at 50 μg/mL for the *S. enterica* serovar Hadar 5643 infection of ileum sections (FIG. 8). 6-log reduction in genome copy number was also achieved with the 1E03 VHH treatment on infection of jejunal sections. 4-log reduction in genome copy number was observed with the 1H07 VHH on infection of jejunum sections. No MIC was determined because no complete inhibition was achieved up to 50 μg/mL. The results represent biological duplicates.

Example 10

Treatment of Broiler Chickens with VHHs

The objective of the study presented in this Example was to test the efficacy of VHH 0A07 in a *Salmonella enterica* challenge model by administration via oral gavage.

Method: Animal testing and data collection was carried out by Colorado Quality Research, Inc. (Wellington, Colo.). Commercial broiler chickens (Cobb 500 breed) were supplied by Simmons Foods™ (Siloam Springs, Ark.). Chicks were received at about 1 day old and put on a non-medicated industry average diet. The birds were housed in concrete floor pens within an environmentally controlled facility. All birds were placed in clean pens containing clean pine shavings as bedding. Lighting was via incandescent lights and a commercial lighting program was used. Water and feed was provided ad libitum throughout the study. The test facility, pens and birds were observed at least twice daily for general flock condition, lighting, water, feed, and ventilation. Upon receipt and prior to placement, all birds were tagged in the back of the neck with uniquely numbered individual identification tags. Clinical observations of all birds were made once daily. These observations included body weight and feed intake measurements.

For the study, 60 one-day old chicks were randomly assigned to one of two treatment groups, Group A or Group B—each group consisting of 30 birds. Group A was the control group; birds within this group received untransformed, inactivated *E. coli* cells. In contrast, Group B birds received inactivated *E. coli* expressing VHH 0A07.

Upon arrival, the chicks were tagged, randomized, weighed, and placed into 6 pens (2 blocks of 3 pens; 10 birds per pen). The following morning, the birds were challenged by oral gavage. Specifically, birds were gavaged with 0.5 ml of *S. enterica* at a concentration of $1.0\times10^8$ CFU/bird. Treatment was thereafter administered three times via oral gavage: at 1 h, 24 h, and 48 h post challenge gavage. Birds in Group A were gavaged with inactivated *E. coli*; Group B with inactivated *E. coli* expressing VHH 0A07 (1.5 mg per dose per bird in 1000 μl $dH_2O$). At 70 h, birds were weighed and euthanized.

Tissue samples were immediately collected from the euthanized birds for microbiological assays. Jejunum and ileum materials were composited into one sample per bird. Collected samples were transported on icepacks to Microbial Research Inc. (Fort Collins, Colo.) for microbiological assays.

Figure 9:
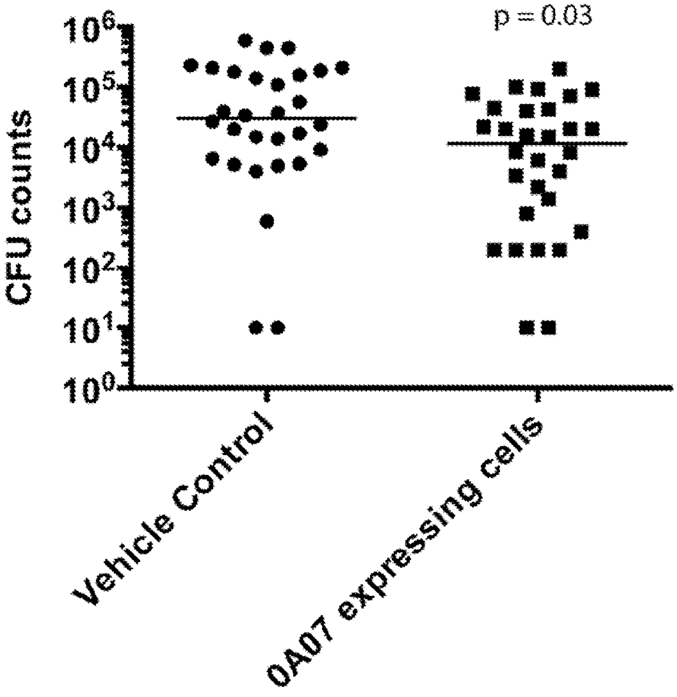
FIG. 9 is a scatter plot showing the effects of administering VHH 0A07 to non-SPF broiler chicks challenged with *S. enterica* serovar Hadar 5643 (CFU counts for ileum and jejunum sections are shown).

Result:

Administration of VHH 0A07 significantly decreased the levels of *Salmonella enterica* serovar Hadar 5643 in chick jejunum and ileum by 0.7 $\log_{10}$ (p=0.029) (FIG. 9). The geometric mean and median of *Salmonella* load in control Group A (not expressing VHH 0A07) was $2.2\times10^4$ and $3.1\times10^4$, respectively. The geometric mean and median of *Salmonella* load in Group B (expressing VHH 0A07) was $5.2\times10^3$ and $1.2\times10^4$, respectively.

TABLES

TABLE 1

Anti-Salmonella VHHs
The following are the numbered clones identified within each class of VHHs.

| Class | Colony |
|---|---|
| 1 | 4E08, 4E12, 4F10, 4G04, 4G10, 4H05 |
| 2 | 4A03, 4A04, 4A07, 4A09, 4A11, 4B01, 4B02, 4H01, 1E08 |
| 3 | 0A09 |
| 4 | 1E10, 0C07, 4C09, 4D02, 4D03, 1C11, 0A11, 2C07, 0A08, 0F11, 0G08, 0G12 |
| 5 | 0G11, 1B08 |
| 6 | 1A08, 1C10, 0A07, 0B08, 0B10, 0B11, 0C11, 0E09, 0E11, 0F12, 0H10 |
| 7 | 1E05 |
| 8 | 2A09 |
| 9 | 0E07, 1B07, 1C08, 1D07, 1D08, 1F10, 1G08, 0A10, 0A12, 0C10, 0D07, 0D09, 0D10, 0E08, 0E12, 0F07, 0G09, 0H11, 0H12 |
| 10 | 3B04, 3B07, 4A05, 4A06, 4E02, 4E06, 4E10, 4E11, 4F02, 4F03, 4F06, 4F09, 4F11, 4G05, 4G06, 4G08, 4G09, 4G11, 4H02, 4H06, 4H08, 4H11, 4H12, 0B07 |
| 11 | 1H07, 0F10, 2A02, 1E11, 3A01, 3A02, 3A03, 3A04, 3A05, 3A06, 3A07, 3A08, 3A09, 3A10, 3A11, 3B01, 3B02, 3B03, 3B05, 3B06, 3B08, 3B09, 3B10, 3B11, 4A01, 4A12, 4B04, 4B05, 4B06, 4B07,, 4B08, 4B09, 4B10, 4B11, 4B12, 4C01, 4C02, 4C03, 4C04, 4C05, 4C06, 4C07, 4C08, 4C11, 4C12, 4D04, 4D05, 4D06, 4D07, 4D08, 4D09, 4D10, 4D12, 4E01, 4E03, 4E04, 4E05, 4E07, 4E09, 4F01, 4F04, 4F05, 4F07, 4F08, 4G02, 4G03, 4G07, 4G12, 4H03, 4H04, 4H07, 4H09, 4H10, 1C09, 1F07, 1F08, 2H05, 0B12, 0D11, 0E10, 0F08, 0G07, 0H07, 0H09, |
| 12 | 1B06, 1E03 |
| 13 | 1G06, 2A07, 2B02, 0C08 |
| 14 | 1G03, 2H10, 0C09, 0D08, 0F09, 0G10, 2B07, 1A07 |
| 15 | 4C10, 4G01 |
| 16 | 4D01, 4D11 |
| 17 | 4F12 |
| 18 | 0D12 |

TABLE 2

Consensus amino acid sequences of CDR1, CDR2 and CDR3 of the five groups of anti-Salmonella VHHs

| CDR1 | | |
|---|---|---|
| Group 1 | $GRX_1FSX_2KP$ | 0A08; 1B08; 0A07; 1E05; 0H12; 1H07; 1E03; 0F09; 4D01; 0D12 |
| Group 2 | GLDFSSYA | 4F10; 1E08; 3B04; 4F12 |
| Group 3 | GIIFSINA | 2A09; 1G06 |
| Group 4 | GRSFSLYG | 0A09 |
| Group 5 | GSIFSGDA | 4C10 |

$X_1$ = T or S; $X_2$ = V or K

TABLE 2-continued

| Consensus amino acid sequences of CDR1, CDR2 and CDR3 of the five groups of anti-Salmonella VHHs | | |
|---|---|---|
| | CDR2 | |
| Group 1 | $ASX_3TGVST$ | 0A08; 1B08; 0A07; 1E05; 0H12; 1H07; 1E03; 0F09; 4D01; 0D12 |
| Group 2 | ISRFGGRL | 4F10; 1E08; 3B04; 4F12 |
| Group 3 | ISAYDHT | 2A09; 1G06 |
| Group 4 | ISGSGLATS | 0A09 |
| Group 5 | IGKEGDT | 4C10 |
| $X_3$ = F or Y | | |
| | CDR3 | |
| Group 1 | $AGTX_4RTLWGSKWRDX_5X_6EYEY$ | 0A08; 1B08; 0A07; 1E05; 0H12; 1H07; 1E03; 0F09; 4D01; 0D12 |
| Group 2 | AADRRSGLGTSKEYDY | 4F10; 1E08; 3B04; 4F12 |
| Group 3 | NVDEIRKF | 2A09; 1G06 |
| Group 4 | AQRWTSGTIARATGEYGY | 0A09 |
| Group 5 | ATFEERPQPSYVY | 4C10 |
| $X_4$ = T or L; $X_5$ = V or R; $X_6$ = L or R | | |

The scope of the claims should not be limited by the preferred embodiments set forth in the examples, but should be given the broadest interpretation consistent with the description as a whole.

REFERENCES

Arbabi-Ghahroudi, M., et al. (2009) Isolation of monoclonal antibody fragments from phage display libraries. Methods Mol Biol. 502:341-64.

Baral, T. N., et al. (2013) Single domain antibodies and their utility. Curr Protoc Immunol. 103:IV:2.17:2.17.1-2.17.57.

Chakchouk-Mtibaa, A., et al. (2014) Characterization of the bacteriocin BacJ1 and its effectiveness for the inactivation of *Salmonella typhimurium* during turkey escalope storage. Food Chem. 152:566-72.

Conrath, K. E., et al. (2003) Emergence and evolution of functional heavy-chain antibodies in Camelidae. Dev Comp Immunol. 27(2):87-103.

Cox, N. A., et al. (2014) Sampling naturally contaminated broiler carcasses for *Salmonella* by three different methods. J Food Prot. 77(3):493-5.

Dougan, G., et al. (1988) Construction and characterization of vaccine strains of *Salmonella* harboring mutations in two different aro genes. J Infect Dis. 158(6):1329-35.

Doyle, M. P., Erickson, M. C. (2006) Reducing the carriage of foodborne pathogens in livestock and poultry. Poult Sci. 85(6):960-73.

Hagihara, Y. et al. (2007) Stabilization of an immunoglobulin fold domain by an engineered disulfide bond at the buried hydrophobic region. J Biol Chem. 14; 282(50): 36489-95.

Hugas, M., Beloeil, P., et al. (2014) Controlling *Salmonella* along the food chain in the European Union—progress over the last ten years. Euro Surveill. 19(19).

Hussack, G., et al. (2011) Engineered single domain antibodies with high protease resistance and thermal stability. PLoS One. 6(11):e28218.

Hussack, G., et al. (2014) Protease-resistant single-domain antibodies inhibit *Campylobacter jejuni* motility. Protein Eng Des Sel. 27(6):191-8.

Kalmokoff, M. (2006) Proteomic analysis of *Campylobacter jejuni* 11168 biofilms reveals a role for the motility complex in biofilm formation. J Bacteriol. 188(12):4312-20.

Lefranc, M. P., et al. (2003) IMGT unique numbering for immunoglobulin and T cell receptor variable domains and Ig superfamily V-like domains. Dev Comp Immunol. 27(1):55-77.

Malorny, B., et al. (2004) Diagnostic Real-Time PCR for Detection of *Salmonella* in Food. Appl Environ Microbiol. 70(12): 7046-7052.

Mazengia, E., et al. (2014) Prevalence, concentrations, and antibiotic sensitivities of *salmonella* serovars in poultry from retail establishments in Seattle, Wash. J Food Prot. 77(6):885-93.

Messens, W., et al. (2013) Estimating the public health impact of setting targets at the European level for the reduction of zoonotic *Salmonella* in certain poultry populations. Int J Environ Res Public Health. 10:4836-50.

Muyldermans, S., et al. (1994) Sequence and structure of $V_H$ domain from naturally occurring camel heavy chain immunoglobulins lacking light chains. Protein Eng. 7(9): 1129-1135.

Muyldermans, S. (2013) Nanobodies: natural single-domain antibodies. Annu Rev Biochem. 82:775-97.

Pace, C. N., et al. (1995) How to measure and predict the molar absorption coefficient of a protein. Protein Sci. (11):2411-2423.

Popoff, M. Y., and L. Le Minor (1997) Antigenic formulas of the *Salmonella* serovars, 7th revision. W.H.O. Collaborating Centre for Reference and Research on *Salmonella*. Institut Pasteur, Paris, France.

Porwollik, et al. (2004) Characterization of *Salmonella enterica* Subspecies I Genovars by Use of Microarrays. J Bacteriol. 186(17):5883-5898.

Ravel, A., et al. (2010) Seasonality in human *salmonellosis*: assessment of human activities and chicken contamination as driving factors. Foodborne Pathog Dis. 7(7):785-94.

Rodriguez, A., et al. (2006) Prevalence of *Salmonella* in diverse environmental farm samples. J Food Prot. 69(11): 2576-80.

Saerens, D., et al. (2008) Disulfide Bond introduction for general stabilization of immunoglobulin heavy-chain variable domains. J Mol Biol. 377(2):478-88.

Waseh, S., et al. (2010) Orally administered P22 phage tailspike protein reduces *salmonella* colonization in chickens: prospects of a novel therapy against bacterial infections. PLoS One 5(11):e13904.

What is claimed is:

1. An isolated antibody or antibody fragment that binds to *Salmonella* comprising a Complementary Determining Region (CDR)1, a CDR2 and a CDR3, wherein the CDR1, CDR2 and CDR3 comprise the following:

(A) (i) the Complementarity Determining Region (CDR)1 comprising an amino acid sequence of $GRX_1FSX_2$ KP (SEQ ID NO: 37); (ii) the CDR2 comprising an amino acid sequence of $ASX_3TGVST$ (SEQ ID NO:38); and (iii) the CDR3 comprising an amino acid sequence of $AGTX_4RTLWGSKWRDX_5X_6EYEY$ (SEQ ID NO:39),wherein is $X_1$ is T or S; $X_2$ is V or K; $X_3$ is F or Y; $X_4$ is T or L; $X_5$ is V or R; and $X_6$ is L or R.

* * * * *

SEQUENCE LISTING

```
<160> NUMBER OF SEQ ID NOS: 60

<210> SEQ ID NO 1
<211> LENGTH: 123
<212> TYPE: PRT
<213> ORGANISM: Vicugna pacos
<220> FEATURE:
<221> NAME/KEY: MISC_FEATURE
<222> LOCATION: (1)..(123)
<223> OTHER INFORMATION: 4E08

<400> SEQUENCE: 1

His Val Gln Leu Val Glu Ser Gly Gly Gly Leu Val Gln Ala Gly Gly
1               5                   10                  15

Ser Leu Arg Leu Ser Cys Ala Ala Ser Gly Leu Asp Phe Ser Ser Tyr
            20                  25                  30

Ala Met Gly Trp Phe Arg Gln Ala Pro Gly Glu Glu Arg Glu Tyr Val
        35                  40                  45

Ala Gly Ile Ser Arg Phe Gly Gly Arg Leu Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr His Cys
                85                  90                  95

Ala Ala Asp Arg Arg Ser Gly Leu Gly Thr Ser Lys Glu Tyr Asp Tyr
            100                 105                 110

Trp Gly Gln Gly Thr Gln Val Thr Val Ser Ser
        115                 120


<210> SEQ ID NO 2
<211> LENGTH: 123
<212> TYPE: PRT
<213> ORGANISM: Vicugna pacos
<220> FEATURE:
<221> NAME/KEY: MISC_FEATURE
<222> LOCATION: (1)..(123)
<223> OTHER INFORMATION: 1E08

<400> SEQUENCE: 2

Gln Val Gln Leu Val Glu Ser Gly Gly Gly Leu Val Gln Ala Gly Gly
1               5                   10                  15

Ser Leu Arg Leu Ser Cys Ala Ala Ser Gly Leu Asp Phe Ser Ser Tyr
            20                  25                  30

Ala Met Gly Trp Phe Arg Gln Ala Pro Gly Glu Glu Arg Glu Tyr Val
        35                  40                  45

Ala Gly Ile Ser Arg Phe Gly Gly Arg Leu Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr His Cys
                85                  90                  95

Ala Ala Asp Arg Arg Ser Gly Leu Gly Thr Ser Lys Glu Tyr Asp Tyr
```

```
            100                 105                 110

Trp Gly Gln Gly Thr Gln Val Thr Val Ser Ser
        115                 120


<210> SEQ ID NO 3
<211> LENGTH: 125
<212> TYPE: PRT
<213> ORGANISM: Vicugna pacos
<220> FEATURE:
<221> NAME/KEY: MISC_FEATURE
<222> LOCATION: (1)..(125)
<223> OTHER INFORMATION: 0A09

<400> SEQUENCE: 3

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Leu Tyr
            20                  25                  30

Gly Met Gly Trp Phe Arg Gln Ala Pro Glu Lys Glu Arg Glu Phe Val
        35                  40                  45

Ala Ala Ile Ser Gly Ser Gly Leu Ala Thr Ser Tyr Val Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gln Arg Trp Thr Ser Gly Thr Ile Ala Arg Ala Thr Gly Glu Tyr
            100                 105                 110

Gly Tyr Trp Gly Gln Gly Thr Gln Val Thr Val Ser Ser
        115                 120                 125


<210> SEQ ID NO 4
<211> LENGTH: 127
<212> TYPE: PRT
<213> ORGANISM: Vicugna pacos
<220> FEATURE:
<221> NAME/KEY: MISC_FEATURE
<222> LOCATION: (1)..(127)
<223> OTHER INFORMATION: 0A08

<400> SEQUENCE: 4

Gln Val Gln Leu Val Glu Ser Gly Gly Gly Leu Val Gln Ala Gly Gly
1               5                   10                  15

Ser Leu Arg Leu Ser Cys Thr Asp Ser Gly Arg Thr Phe Ser Val Lys
            20                  25                  30

Pro Met Gly Trp Phe Arg Gln Ala Pro Gly Lys Glu Arg Glu Phe Val
        35                  40                  45

Ala Ala Ala Ser Phe Thr Gly Val Ser Thr Phe Tyr Ala Asp Ser Val
    50                  55                  60

Lys Asp Arg Phe Thr Ile Phe Arg Asp Lys Asp Lys Asn Ala Met Asp
65                  70                  75                  80

Leu Gln Ile Asn Ser Leu Lys Pro Glu Asp Thr Gly Ala Tyr Tyr Cys
                85                  90                  95

Ala Gly Thr Thr Arg Thr Leu Trp Gly Ser Lys Trp Arg Asp Val Leu
            100                 105                 110

Glu Tyr Glu Tyr Trp Gly Gln Gly Thr Gln Val Thr Val Ser Ser
        115                 120                 125


<210> SEQ ID NO 5
```

<211> LENGTH: 127
<212> TYPE: PRT
<213> ORGANISM: Vicugna pacos
<220> FEATURE:
<221> NAME/KEY: MISC_FEATURE
<222> LOCATION: (1)..(127)
<223> OTHER INFORMATION: 1B08

<400> SEQUENCE: 5

```
Gln Val Gln Leu Val Glu Ser Gly Gly Gly Leu Val Gln Ala Gly Gly
1               5                   10                  15

Ser Leu Arg Leu Ser Cys Thr Asp Ser Gly Arg Thr Phe Ser Val Lys
            20                  25                  30

Pro Met Gly Trp Phe Arg Gln Ala Pro Gly Met Glu Arg Glu Phe Val
        35                  40                  45

Ala Ala Ala Ser Phe Thr Gly Val Ser Thr Phe Tyr Ala Asp Ser Val
    50                  55                  60

Lys Asp Arg Phe Ala Ile Phe Arg Asp Lys Asp Lys Asn Thr Met Asp
65                  70                  75                  80

Leu Gln Ile Asn Ser Leu Lys Pro Glu Asp Thr Gly Ala Tyr Tyr Cys
                85                  90                  95

Ala Gly Thr Thr Arg Thr Leu Trp Gly Ser Lys Trp Arg Asp Val Leu
            100                 105                 110

Glu Tyr Glu Tyr Trp Gly Gln Gly Thr Gln Val Thr Val Ser Ser
        115                 120                 125
```

<210> SEQ ID NO 6
<211> LENGTH: 127
<212> TYPE: PRT
<213> ORGANISM: Vicugna pacos
<220> FEATURE:
<221> NAME/KEY: MISC_FEATURE
<222> LOCATION: (1)..(127)
<223> OTHER INFORMATION: 0A07

<400> SEQUENCE: 6

```
Gln Val Gln Leu Val Glu Ser Gly Gly Gly Leu Val Gln Ala Gly Gly
1               5                   10                  15

Ser Leu Arg Leu Ser Cys Thr Asp Ser Gly Arg Thr Phe Ser Val Lys
            20                  25                  30

Pro Met Gly Trp Phe Arg Gln Ala Pro Gly Met Glu Arg Glu Phe Val
        35                  40                  45

Ala Ala Ala Ser Phe Thr Gly Val Ser Thr Phe Tyr Ala Asp Ser Val
    50                  55                  60

Lys Asp Arg Phe Thr Ile Phe Arg Asp Lys Asp Lys Asn Thr Met Asp
65                  70                  75                  80

Leu Gln Ile Asn Ser Leu Lys Pro Glu Asp Thr Gly Ala Tyr Tyr Cys
                85                  90                  95

Ala Gly Thr Thr Arg Thr Leu Trp Gly Ser Lys Trp Arg Asp Val Leu
            100                 105                 110

Glu Tyr Glu Tyr Trp Gly Gln Gly Thr Gln Val Thr Val Ser Ser
        115                 120                 125
```

<210> SEQ ID NO 7
<211> LENGTH: 127
<212> TYPE: PRT
<213> ORGANISM: Vicugna pacos
<220> FEATURE:
<221> NAME/KEY: MISC_FEATURE
<222> LOCATION: (1)..(127)
<223> OTHER INFORMATION: 1E05

<400> SEQUENCE: 7

```
Gln Val Gln Leu Val Glu Ser Gly Gly Gly Leu Val Gln Ala Gly Gly
1               5                   10                  15

Ser Leu Ser Leu Ser Cys Glu Asp Ser Gly Arg Ser Phe Ser Val Lys
            20                  25                  30

Pro Met Ala Trp Phe Arg Gln Ala Pro Gly Leu Glu Arg Glu Phe Val
        35                  40                  45

Ala Ala Ala Ser Phe Thr Gly Val Ser Thr Phe Tyr Ala Asp Ser Val
    50                  55                  60

Lys Asp Arg Tyr Thr Ile Phe Arg Glu Lys Asp Asn Asn Thr Val Tyr
65                  70                  75                  80

Leu Gln Met Asn Ser Leu Gln Pro Glu Asp Thr Gly Ala Tyr Tyr Cys
                85                  90                  95

Ala Gly Thr Leu Arg Thr Leu Trp Gly Ser Lys Trp Arg Asp Arg Arg
            100                 105                 110

Glu Tyr Glu Tyr Trp Gly Gln Gly Thr Gln Val Thr Val Ser Ser
        115                 120                 125
```

<210> SEQ ID NO 8
<211> LENGTH: 114
<212> TYPE: PRT
<213> ORGANISM: Vicugna pacos
<220> FEATURE:
<221> NAME/KEY: MISC_FEATURE
<222> LOCATION: (1)..(114)
<223> OTHER INFORMATION: 2A09

<400> SEQUENCE: 8

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ile Ile Phe Ser Ile Asn
            20                  25                  30

Ala Met Gly Trp Tyr Arg Gln Ala Pro Gly Lys Gln Arg Glu Leu Val
        35                  40                  45

Ala Arg Ile Ser Ala Tyr Asp His Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Asp Glu Ile Arg Lys Phe Trp Gly Gln Gly Thr Gln Val Thr Val
            100                 105                 110

Ser Ser
```

<210> SEQ ID NO 9
<211> LENGTH: 127
<212> TYPE: PRT
<213> ORGANISM: Vicugna pacos
<220> FEATURE:
<221> NAME/KEY: MISC_FEATURE
<222> LOCATION: (1)..(127)
<223> OTHER INFORMATION: 0H12

<400> SEQUENCE: 9

```
Gln Val Gln Leu Val Glu Ser Gly Gly Gly Leu Val Gln Pro Gly Gly
1               5                   10                  15

Ser Leu Arg Leu Ser Cys Thr Asp Ser Gly Arg Thr Phe Ser Val Lys
            20                  25                  30
```

```
Pro Met Gly Trp Phe Arg Gln Ala Pro Gly Met Glu Arg Glu Phe Val
        35                  40                  45

Ala Ala Ala Ser Phe Thr Gly Val Ser Thr Phe Tyr Ala Asp Ser Val
    50                  55                  60

Lys Asp Arg Phe Thr Ile Phe Arg Asp Lys Asp Lys Asn Thr Met Asp
65                  70                  75                  80

Leu Gln Ile Asn Ser Leu Lys Pro Glu Asp Thr Gly Ala Tyr Tyr Cys
                85                  90                  95

Ala Gly Thr Thr Arg Thr Leu Trp Gly Ser Lys Trp Arg Asp Val Leu
            100                 105                 110

Glu Tyr Glu Tyr Trp Gly Gln Gly Thr Gln Val Thr Val Ser Ser
        115                 120                 125
```

<210> SEQ ID NO 10
<211> LENGTH: 123
<212> TYPE: PRT
<213> ORGANISM: Vicugna pacos
<220> FEATURE:
<221> NAME/KEY: MISC_FEATURE
<222> LOCATION: (1)..(123)
<223> OTHER INFORMATION: 3B04

<400> SEQUENCE: 10

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Leu Asp Phe Ser Ser Tyr
            20                  25                  30

Ala Met Gly Trp Phe Arg Gln Ala Pro Gly Glu Glu Arg Glu Tyr Val
        35                  40                  45

Ala Gly Ile Ser Arg Phe Gly Gly Arg Leu Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr His Cys
                85                  90                  95

Ala Ala Asp Arg Arg Ser Gly Leu Gly Thr Ser Lys Glu Tyr Asp Tyr
            100                 105                 110

Trp Gly Gln Gly Thr Gln Val Thr Val Ser Ser
        115                 120
```

<210> SEQ ID NO 11
<211> LENGTH: 127
<212> TYPE: PRT
<213> ORGANISM: Vicugna pacos
<220> FEATURE:
<221> NAME/KEY: MISC_FEATURE
<222> LOCATION: (1)..(127)
<223> OTHER INFORMATION: 1H07

<400> SEQUENCE: 11

```
Gln Val Lys Leu Glu Glu Ser Gly Gly Gly Leu Val Gln Ala Gly Gly
1               5                   10                  15

Ser Leu Arg Leu Ser Cys Thr Asp Ser Gly Arg Thr Phe Ser Lys Lys
            20                  25                  30

Pro Met Gly Trp Phe Arg Gln Ala Pro Gly Met Glu Arg Glu Phe Val
        35                  40                  45

Ala Ala Ala Ser Tyr Thr Gly Val Ser Thr Phe Tyr Ala Asp Ser Val
    50                  55                  60
```

-continued

Lys Asp Arg Phe Thr Ile Phe Arg Asp Lys Asp Lys Asn Thr Met Asp
65 70 75 80

Leu Gln Ile Asn Ser Leu Lys Pro Glu Asp Thr Gly Ala Tyr Tyr Cys
85 90 95

Ala Gly Thr Thr Arg Thr Leu Trp Gly Ser Lys Trp Arg Asp Val Leu
100 105 110

Glu Tyr Glu Tyr Trp Gly Gln Gly Thr Gln Val Thr Val Ser Ser
115 120 125

<210> SEQ ID NO 12
<211> LENGTH: 127
<212> TYPE: PRT
<213> ORGANISM: Vicugna pacos
<220> FEATURE:
<221> NAME/KEY: MISC_FEATURE
<222> LOCATION: (1)..(127)
<223> OTHER INFORMATION: 1E03

<400> SEQUENCE: 12

Gln Val Lys Leu Glu Glu Ser Gly Gly Gly Leu Val Gln Ala Gly Gly
1 5 10 15

Ser Leu Ser Leu Ser Cys Glu Asp Ser Gly Arg Ser Phe Ser Val Lys
20 25 30

Pro Met Ala Trp Phe Arg Gln Ala Pro Gly Leu Glu Arg Glu Phe Val
35 40 45

Ala Ala Ala Ser Phe Thr Gly Val Ser Thr Phe Tyr Ala Asp Ser Val
50 55 60

Lys Asp Arg Tyr Thr Ile Phe Arg Glu Lys Asp Asn Asn Thr Val Tyr
65 70 75 80

Leu Gln Met Asn Ser Leu Gln Pro Glu Asp Thr Gly Ala Tyr Tyr Cys
85 90 95

Ala Gly Thr Leu Arg Thr Leu Trp Gly Ser Lys Trp Arg Asp Arg Arg
100 105 110

Glu Tyr Glu Tyr Trp Gly Gln Gly Thr Gln Val Thr Val Ser Ser
115 120 125

<210> SEQ ID NO 13
<211> LENGTH: 114
<212> TYPE: PRT
<213> ORGANISM: Vicugna pacos
<220> FEATURE:
<221> NAME/KEY: MISC_FEATURE
<222> LOCATION: (1)..(114)
<223> OTHER INFORMATION: 1G06

<400> SEQUENCE: 13

Gln Val Lys Leu Glu Glu Ser Gly Gly Gly Leu Val Gln Pro Gly Gly
1 5 10 15

Ser Leu Arg Leu Ser Cys Ala Ala Ser Gly Ile Ile Phe Ser Ile Asn
20 25 30

Ala Met Gly Trp Tyr Arg Gln Ala Pro Gly Lys Gln Arg Glu Leu Val
35 40 45

Ala Arg Ile Ser Ala Tyr Asp His Thr Asn Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Asn
85 90 95

Val Asp Glu Ile Arg Lys Phe Trp Gly Gln Gly Thr Gln Val Thr Val

```
            100                 105                 110

Ser Ser


<210> SEQ ID NO 14
<211> LENGTH: 127
<212> TYPE: PRT
<213> ORGANISM: Vicugna pacos
<220> FEATURE:
<221> NAME/KEY: MISC_FEATURE
<222> LOCATION: (1)..(127)
<223> OTHER INFORMATION: 1A07

<400> SEQUENCE: 14

Gln Val Lys Leu Glu Glu Ser Gly Gly Gly Leu Val Gln Pro Gly Gly
1               5                   10                  15

Ser Leu Arg Leu Ser Cys Thr Asp Ser Gly Arg Thr Phe Ser Val Lys
            20                  25                  30

Pro Met Gly Trp Phe Arg Gln Ala Pro Gly Met Glu Arg Glu Phe Val
        35                  40                  45

Ala Ala Ala Ser Phe Thr Gly Val Ser Thr Phe Tyr Ala Asp Ser Val
    50                  55                  60

Lys Asp Arg Phe Thr Ile Phe Arg Asp Lys Asp Lys Asn Thr Met Asp
65                  70                  75                  80

Leu Gln Ile Asn Ser Leu Lys Pro Glu Asp Thr Gly Ala Tyr Tyr Cys
                85                  90                  95

Ala Gly Thr Thr Arg Thr Leu Trp Gly Ser Lys Trp Arg Asp Val Leu
            100                 105                 110

Glu Tyr Glu Tyr Trp Gly Gln Gly Thr Gln Val Thr Val Ser Ser
        115                 120                 125


<210> SEQ ID NO 15
<211> LENGTH: 119
<212> TYPE: PRT
<213> ORGANISM: Vicugna pacos
<220> FEATURE:
<221> NAME/KEY: MISC_FEATURE
<222> LOCATION: (1)..(119)
<223> OTHER INFORMATION: 4C10

<400> SEQUENCE: 15

Gln Val Lys Leu Glu Glu Ser Gly Gly Gly Ser Val Gln Ala Gly Gly
1               5                   10                  15

Ser Leu Arg Leu Ser Cys Ala Val Ser Gly Ser Ile Phe Ser Gly Asp
            20                  25                  30

Ala Met Gly Trp Tyr Arg Gln Ala Pro Gly Lys Lys Arg Glu Tyr Val
        35                  40                  45

Ala Leu Ile Gly Lys Glu Gly Asp Thr Val Tyr Ala Asp Ser Val Lys
    50                  55                  60

Gly Arg Phe Thr Ile Ser Arg Asp Asn Ala Lys Asn Thr Phe Tyr Leu
65                  70                  75                  80

Gln Met Asn Asn Leu Glu Pro Glu Asp Thr Ala Arg Tyr Ile Cys Ala
                85                  90                  95

Thr Phe Glu Glu Arg Pro Gln Pro Ser Tyr Val Tyr Trp Gly Pro Gly
            100                 105                 110

Thr Gln Val Thr Val Ser Ser
        115


<210> SEQ ID NO 16
<211> LENGTH: 127
```

<212> TYPE: PRT
<213> ORGANISM: Vicugna pacos
<220> FEATURE:
<221> NAME/KEY: MISC_FEATURE
<222> LOCATION: (1)..(127)
<223> OTHER INFORMATION: 4D01

<400> SEQUENCE: 16

```
Gln Val Lys Leu Val Asp Ser Gly Gly Gly Leu Val Gln Ala Gly Gly
1               5                   10                  15

Ser Leu Arg Leu Ser Cys Thr Asp Ser Gly Arg Thr Phe Ser Lys Lys
            20                  25                  30

Pro Met Gly Trp Phe Arg Gln Ala Pro Gly Met Glu Arg Glu Phe Val
        35                  40                  45

Ala Ala Ala Ser Tyr Thr Gly Val Ser Thr Phe Tyr Ala Asp Ser Val
    50                  55                  60

Lys Asp Arg Phe Thr Ile Phe Arg Asp Lys Asp Lys Asn Thr Met Asp
65                  70                  75                  80

Leu Gln Ile Asn Ser Leu Lys Pro Glu Asp Thr Gly Ala Tyr Tyr Cys
                85                  90                  95

Ala Gly Thr Thr Arg Thr Leu Trp Gly Ser Lys Trp Arg Asp Val Leu
            100                 105                 110

Glu Tyr Glu Tyr Trp Gly Gln Gly Thr Gln Val Thr Val Ser Ser
        115                 120                 125
```

<210> SEQ ID NO 17
<211> LENGTH: 123
<212> TYPE: PRT
<213> ORGANISM: Vicugna pacos
<220> FEATURE:
<221> NAME/KEY: MISC_FEATURE
<222> LOCATION: (1)..(123)
<223> OTHER INFORMATION: 4F12

<400> SEQUENCE: 17

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Leu Asp Phe Ser Ser Tyr
            20                  25                  30

Ala Met Gly Trp Phe Arg Gln Ala Pro Gly Glu Glu Arg Glu Tyr Val
        35                  40                  45

Ala Gly Ile Ser Arg Phe Gly Gly Arg Leu Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr His Cys
                85                  90                  95

Ala Ala Asp Arg Arg Ser Gly Leu Gly Thr Ser Lys Glu Tyr Asp Tyr
            100                 105                 110

Trp Gly Gln Gly Thr Gln Val Thr Val Ser Ser
        115                 120
```

<210> SEQ ID NO 18
<211> LENGTH: 127
<212> TYPE: PRT
<213> ORGANISM: Vicugna pacos
<220> FEATURE:
<221> NAME/KEY: MISC_FEATURE
<222> LOCATION: (1)..(127)
<223> OTHER INFORMATION: 0D12

<400> SEQUENCE: 18

Gln Val Gln Leu Val Glu Ser Gly Gly Gly Leu Val Gln Ala Gly Gly
1               5                   10                  15

Ser Leu Arg Leu Ser Cys Thr Asp Ser Gly Arg Thr Phe Ser Lys Lys
            20                  25                  30

Pro Met Gly Trp Phe Arg Gln Ala Pro Gly Met Glu Arg Glu Phe Val
        35                  40                  45

Ala Ala Ala Ser Tyr Thr Gly Val Ser Thr Phe Tyr Ala Asp Ser Val
    50                  55                  60

Lys Asp Arg Phe Thr Ile Ser Arg Asp Lys Asp Lys Asn Thr Met Asp
65                  70                  75                  80

Leu Gln Ile Asn Ser Leu Lys Pro Glu Asp Thr Gly Ala Tyr Tyr Cys
                85                  90                  95

Ala Gly Thr Thr Arg Thr Leu Trp Gly Ser Lys Trp Arg Asp Val Leu
            100                 105                 110

Glu Tyr Glu Tyr Trp Gly Gln Gly Thr Gln Val Thr Val Ser Ser
        115                 120                 125

<210> SEQ ID NO 19
<211> LENGTH: 369
<212> TYPE: DNA
<213> ORGANISM: Vicugna pacos
<220> FEATURE:
<221> NAME/KEY: misc_feature
<222> LOCATION: (1)..(369)
<223> OTHER INFORMATION: 4E08

<400> SEQUENCE: 19
catgtgcagc tggtggagtc tgggggagga ttggtgcagg ctgggggctc tctgagactc 60
tcctgtgcag cctctggact ggacttcagt agctatgcca tgggctggtt ccgccaggct 120
ccaggagagg agcgtgagta cgtagcaggt attagtagat ttggtggtag gctctactat 180
gcagactccg tgaagggccg attcaccatc tccagagaca acgccaagaa cacggtgtat 240
ctgcaaatga acagtctgaa acctgaggac acggccattt atcactgtgc agccgataga 300
cggtcggggt tggggaccag taaggagtat gactactggg gccaggggac ccaggtcacc 360
gtctcctca 369

<210> SEQ ID NO 20
<211> LENGTH: 375
<212> TYPE: DNA
<213> ORGANISM: Vicugna pacos
<220> FEATURE:
<221> NAME/KEY: misc_feature
<222> LOCATION: (1)..(375)
<223> OTHER INFORMATION: 1E08

<400> SEQUENCE: 20
caggctcagg tacagctggt ggagtctggg ggaggattgg tgcaggctgg gggctctctg 60
agactctcct gtgcagcctc tggactggac ttcagtagct atgccatggg ctggttccgc 120
caggctccag gagaggagcg tgagtacgta gcaggtatta gtagatttgg tggtaggctc 180
tactatgcag actccgtgaa gggccgattc accatctcca gagacaacgc caagaacacg 240
gtgtatctgc aaatgaacag tctgaaacct gaggacacgg ccatttatca ctgtgcagcc 300
gatagacggt cggggttggg gaccagtaag gagtatgact actggggcca ggggacccag 360
gtcaccgtct cctca 375

<210> SEQ ID NO 21
<211> LENGTH: 381
<212> TYPE: DNA
<213> ORGANISM: Vicugna pacos
<220> FEATURE:
<221> NAME/KEY: misc_feature
<222> LOCATION: (1)..(381)
<223> OTHER INFORMATION: 0A09

<400> SEQUENCE: 21
caggctcagg tacagctggt ggagtctggg ggaggattgg tgcaggctgg ggggtctctg 60
agactctcct gtgcagcctc tggacgcagc ttcagtcttt atggcatggg ctggttccgc 120
caggctccag agaaggagcg tgagtttgta gcagctatta gcgggagtgg acttgcgaca 180
agttatgtag actccgtgaa gggccgattc accatctcca gagacaacgc caagaacacg 240
gtgtatctgc aaatgaacag cctgaaacct gaggacacgg ccgtttatta ctgtgcccag 300
agatggacca gcggcactat agcgagagcc acgggggagt atggctactg gggccagggg 360
acccaggtca ccgtctcctc a 381

<210> SEQ ID NO 22
<211> LENGTH: 387
<212> TYPE: DNA
<213> ORGANISM: Vicugna pacos
<220> FEATURE:
<221> NAME/KEY: misc_feature
<222> LOCATION: (1)..(387)
<223> OTHER INFORMATION: 0A08

<400> SEQUENCE: 22
caggctcagg tacagctggt ggagtctggg ggaggattgg tgcaggctgg gggctctctg 60
agactctcct gtacagactc tggacgcacc ttcagtgtaa aacccatggg ctggttccgg 120
caggctccag ggaaggagcg tgagtttgta gcagctgcaa gttttactgg tgtgagcaca 180
ttctacgcag actccgtgaa ggaccgattc accatcttcc gagacaagga caagaacgcg 240
atggatctgc aaattaacag cctgaaacct gaggacacgg gcgcgtatta ctgtgcagga 300
accacccgaa cattatgggg tagtaaatgg agagatgttc ttgaatacga atattggggc 360
caggggaccc aggtcaccgt ctcctca 387

<210> SEQ ID NO 23
<211> LENGTH: 387
<212> TYPE: DNA
<213> ORGANISM: Vicugna pacos
<220> FEATURE:
<221> NAME/KEY: misc_feature
<222> LOCATION: (1)..(387)
<223> OTHER INFORMATION: 1B08

<400> SEQUENCE: 23
caggctcagg tacagctggt ggagtctggg ggaggcttgg tgcaggctgg gggctctctg 60
agactctcct gtacagactc tggacgcacc ttcagtgtaa aacccatggg ctggttccgg 120
caggctccag ggatggagcg tgagtttgta gcagctgcaa gttttactgg tgtgagcaca 180
ttctacgcag actccgtgaa ggaccgattc gccatcttcc gagacaagga caagaacacg 240
atggatctgc aaattaacag cctgaaacct gaggacacgg gcgcgtatta ctgtgcagga 300
accacccgaa cattatgggg tagtaaatgg agagatgttc ttgaatacga atattggggc 360
caggggaccc aggtcaccgt ctcctca 387

<210> SEQ ID NO 24

<211> LENGTH: 387
<212> TYPE: DNA
<213> ORGANISM: Vicugna pacos
<220> FEATURE:
<221> NAME/KEY: misc_feature
<222> LOCATION: (1)..(387)
<223> OTHER INFORMATION: 0A07

<400> SEQUENCE: 24
caggctcagg tacagctggt ggagtctggg ggaggattgg tgcaggctgg gggctctctg 60
agactctcct gtacagactc tggacgcacc ttcagtgtaa aacccatggg ctggttccgg 120
caggctccag ggatggagcg tgagtttgta gcagctgcaa gttttactgg tgtgagcaca 180
ttctacgcag actccgtgaa ggaccgattc accatcttcc gagacaagga caagaacacg 240
atggatctgc aaattaacag cctgaaacct gaggacacgg gcgcgtatta ctgtgcagga 300
accacccgaa cattatgggg tagtaaatgg agagatgttc ttgaatacga atattggggc 360
caggggaccc aggtcaccgt ctcctca 387

<210> SEQ ID NO 25
<211> LENGTH: 387
<212> TYPE: DNA
<213> ORGANISM: Vicugna pacos
<220> FEATURE:
<221> NAME/KEY: misc_feature
<222> LOCATION: (1)..(387)
<223> OTHER INFORMATION: 1E05

<400> SEQUENCE: 25
caggctcagg tacagctggt ggagtctggg gggggattgg tgcaggctgg gggctctctg 60
agtctctcct gcgaagactc tggacgctcc ttcagtgtaa agcccatggc ctggttccgg 120
caggctccag ggctggagcg tgagtttgta gcagctgcaa gtttcactgg tgtgagcaca 180
ttctatgcag actccgtgaa ggaccgatac accatcttca gagagaagga caataacacg 240
gtgtatctgc aaatgaacag cctacaacct gaggacacgg gcgcgtatta ttgtgcagga 300
accctccgaa cgctatgggg tagtaaatgg cgggatcgtc gtgaatacga atattggggc 360
caggggaccc aggtcaccgt ctcctca 387

<210> SEQ ID NO 26
<211> LENGTH: 348
<212> TYPE: DNA
<213> ORGANISM: Vicugna pacos
<220> FEATURE:
<221> NAME/KEY: misc_feature
<222> LOCATION: (1)..(348)
<223> OTHER INFORMATION: 2A09

<400> SEQUENCE: 26
caggctcagg tacagctggt ggagtctggg ggaggcttgg tgcagcctgg ggggtctctg 60
agactctcct gtgcagcctc tggaattatc ttcagtatca atgccatggg gtggtatcgc 120
caggctccag ggaagcagcg cgagttggtc gcacgtatta gtgcttatga tcatacaaac 180
tatgcagact ccgtgaaggg ccgattcacc atctccagag acaacgccaa gaacacggtg 240
tatctgcaaa tgaacagcct gaaacctgag gacacggccg tctattactg taatgtagat 300
gaaatacgga aattctgggg ccaggggacc caggtcaccg tctcctca 348

<210> SEQ ID NO 27
<211> LENGTH: 387
<212> TYPE: DNA
<213> ORGANISM: Vicugna pacos
<220> FEATURE:
<221> NAME/KEY: misc_feature
<222> LOCATION: (1)..(387)
<223> OTHER INFORMATION: 0H12

<400> SEQUENCE: 27
caggctcagg tacagctggt ggagtctggg ggaggcttgg tgcagcctgg ggggtctctg 60
agactctcct gtacagactc tggacgcacc ttcagtgtaa aacccatggg ctggttccgg 120
caggctccag ggatggagcg tgagtttgta gcagctgcaa gttttactgg tgtgagcaca 180
ttctacgcag actccgtgaa ggaccgattc accatcttcc gagacaagga caagaacacg 240
atggatctgc aaattaacag cctgaaacct gaggacacgg gcgcgtatta ctgtgcagga 300
accacccgaa cattatgggg tagtaaatgg agagatgttc ttgaatacga atattggggc 360
caggggaccc aggtcaccgt ctcctca 387

<210> SEQ ID NO 28
<211> LENGTH: 369
<212> TYPE: DNA
<213> ORGANISM: Vicugna pacos
<220> FEATURE:
<221> NAME/KEY: misc_feature
<222> LOCATION: (1)..(369)
<223> OTHER INFORMATION: 3B04

<400> SEQUENCE: 28
caggtaaagc tggaggagtc tgggggagga ttggtgcagg ctgggggctc tctgagactc 60
tcctgtgcag cctctggact ggacttcagt agctatgcca tgggctggtt ccgccaggct 120
ccaggagagg agcgtgagta cgtagcaggt attagtagat ttggtggtag gctctactat 180
gcagactccg tgaagggccg attcaccatc tccagagaca acgccaagaa cacggtgtat 240
ctgcaaatga acagtctgaa acctgaggac acggccattt atcactgtgc agccgataga 300
cggtcggggt tggggaccag taaggagtat gactactggg gccaggggac ccaggtcacc 360
gtctcctca 369

<210> SEQ ID NO 29
<211> LENGTH: 381
<212> TYPE: DNA
<213> ORGANISM: Vicugna pacos
<220> FEATURE:
<221> NAME/KEY: misc_feature
<222> LOCATION: (1)..(381)
<223> OTHER INFORMATION: 1H07

<400> SEQUENCE: 29
caggtaaagc tggaggagtc tgggggagga ttggtgcagg ctgggggctc tctgagactc 60
tcctgtacag actctggacg caccttcagt aaaaaaccca tgggctggtt ccggcaggct 120
ccagggatgg agcgtgagtt tgtagcagct gcaagttata ctggtgtgag cacattctat 180
gcagactccg tgaaggaccg attcaccatc ttcagagaca aggacaagaa cacgatggat 240
ctgcaaatta acagcctgaa acctgaggac acgggcgcgt attattgtgc aggaaccacc 300
cgaacattat ggggtagtaa atggcgagat gtccttgaat acgaatattg gggccagggg 360
acccaggtca ccgtctcctc a 381

<210> SEQ ID NO 30
<211> LENGTH: 381
<212> TYPE: DNA
<213> ORGANISM: Vicugna pacos
<220> FEATURE:

<221> NAME/KEY: misc_feature
<222> LOCATION: (1)..(381)
<223> OTHER INFORMATION: 1E03

<400> SEQUENCE: 30
caggtaaagc tggaggagtc tgggggagga ttggtgcagg ctgggggctc tctgagtctc 60
tcctgcgaag actctggacg ctccttcagt gtaaagccca tggcctggtt ccggcaggct 120
ccagggctgg agcgtgagtt tgtagcagct gcaagtttca ctggtgtgag cacattctat 180
gcagactccg tgaaggaccg atacaccatc ttcagagaga aggacaataa cacggtgtat 240
ctgcaaatga acagcctaca acctgaggac acgggcgcgt attattgtgc aggaaccctc 300
cgaacgctat ggggtagtaa atggcgggat cgtcgtgaat acgaatattg gggccagggg 360
acccaggtca ccgtctcctc a 381

<210> SEQ ID NO 31
<211> LENGTH: 342
<212> TYPE: DNA
<213> ORGANISM: Vicugna pacos
<220> FEATURE:
<221> NAME/KEY: misc_feature
<222> LOCATION: (1)..(342)
<223> OTHER INFORMATION: 1G06

<400> SEQUENCE: 31
caggtaaagc tggaggagtc tgggggaggc ttggtgcagc ctggggggtc tctgagactc 60
tcctgtgcag cctctggaat tatcttcagt atcaatgcca tggggtggta tcgccaggct 120
ccagggaagc agcgcgagtt ggtcgcacgt attagtgctt atgatcatac aaactatgca 180
gactccgtga agggccgatt caccatctcc agagacaacg ccaagaacac ggtgtatctg 240
caaatgaaca gcctgaaacc tgaggacacg gccgtctatt actgtaatgt agatgaaata 300
cggaaattct ggggccaggg gacccaggtc accgtctcct ca 342

<210> SEQ ID NO 32
<211> LENGTH: 381
<212> TYPE: DNA
<213> ORGANISM: Vicugna pacos
<220> FEATURE:
<221> NAME/KEY: misc_feature
<222> LOCATION: (1)..(381)
<223> OTHER INFORMATION: 1A07

<400> SEQUENCE: 32
caggtaaagc tggaggagtc tgggggaggc ttggtgcagc ctggggggtc tctgagactc 60
tcctgtacag actctggacg caccttcagt gtaaaaccca tgggctggtt ccggcaggct 120
ccagggatgg agcgtgagtt tgtagcagct gcaagtttta ctggtgtgag cacattctac 180
gcagactccg tgaaggaccg attcaccatc ttccgagaca aggacaagaa cacgatggat 240
ctgcaaatta acagcctgaa acctgaggac acgggcgcgt attactgtgc aggaaccacc 300
cgaacattat ggggtagtaa atggagagat gttcttgaat acgaatattg gggccagggg 360
acccaggtca ccgtctcctc a 381

<210> SEQ ID NO 33
<211> LENGTH: 357
<212> TYPE: DNA
<213> ORGANISM: Vicugna pacos
<220> FEATURE:
<221> NAME/KEY: misc_feature
<222> LOCATION: (1)..(357)
<223> OTHER INFORMATION: 4C10

<400> SEQUENCE: 33
caggtaaagc tggaggagtc tgggggaggc tcggtgcagg ctggggggtc tctgagactc 60
tcctgtgcag tctctggaag catcttcagt ggtgatgcca tgggctggta ccgccaggct 120
ccaggaaaga agcgcgagta tgtcgcgtta attggtaagg aaggtgacac agtctacgca 180
gactctgtga agggccgctt caccatctcc agagacaatg ccaagaacac gttctatcta 240
caaatgaaca acctggaacc tgaggacacg gccagatata tttgtgcgac attcgaggag 300
cgaccccaac catcgtatgt ctactggggc ccggggaccc aggtcaccgt ctcctca 357

<210> SEQ ID NO 34
<211> LENGTH: 381
<212> TYPE: DNA
<213> ORGANISM: Vicugna pacos
<220> FEATURE:
<221> NAME/KEY: misc_feature
<222> LOCATION: (1)..(381)
<223> OTHER INFORMATION: 4D01

<400> SEQUENCE: 34
caggtaaagc tggtggattc tgggggagga ttggtgcagg ctgggggctc tctgagactc 60
tcctgtacag actctggacg caccttcagt aaaaaaccca tgggctggtt ccggcaggct 120
ccagggatgg agcgtgagtt tgtagcagct gcaagttata ctggtgtgag cacattctat 180
gcagactccg tgaaggaccg attcaccatc ttcagagaca aggacaagaa cacgatggat 240
ctgcaaatta acagcctgaa acctgaggac acgggcgcgt attattgtgc aggaaccacc 300
cgaacattat ggggtagtaa atggcgagat gtccttgaat acgaatattg gggccagggg 360
acccaggtca ccgtctcctc a 381

<210> SEQ ID NO 35
<211> LENGTH: 369
<212> TYPE: DNA
<213> ORGANISM: Vicugna pacos
<220> FEATURE:
<221> NAME/KEY: misc_feature
<222> LOCATION: (1)..(369)
<223> OTHER INFORMATION: 4F12

<400> SEQUENCE: 35
caggtgcagc tggtggagtc tgggggagga ttggtgcagg ctgggggctc tctgagactc 60
tcctgtgcag cctctggact ggacttcagt agctatgcca tgggctggtt ccgccaggct 120
ccaggagagg agcgtgagta cgtagcaggt attagtagat ttggtggtag gctctactat 180
gcagactccg tgaagggccg attcaccatc tccagagaca acgccaagaa cacggtgtat 240
ctgcaaatga acagtctgaa acctgaggac acggccattt atcactgtgc agccgataga 300
cggtcggggt tggggaccag taaggagtat gactactggg gccaggggac ccaggtcacc 360
gtctcctca 369

<210> SEQ ID NO 36
<211> LENGTH: 381
<212> TYPE: DNA
<213> ORGANISM: Vicugna pacos
<220> FEATURE:
<221> NAME/KEY: misc_feature
<222> LOCATION: (1)..(381)
<223> OTHER INFORMATION: OD12

<400> SEQUENCE: 36

-continued

```
caggtgcagc tggtggagtc tgggggagga ttggtgcagg ctgggggctc tctgagactc     60

tcctgtacag actctggacg caccttcagt aaaaaaccca tgggctggtt ccggcaggct    120

ccagggatgg agcgtgagtt tgtagcagct gcaagttata ctggtgtgag cacattctat    180

gcagactccg tgaaggaccg attcaccatc tccagagaca aggacaagaa cacgatggat    240

ctgcaaatta acagcctgaa acctgaggac acgggcgcgt attattgtgc aggaaccacc    300

cgaacattat ggggtagtaa atggcgagat gtccttgaat acgaatattg gggccagggg    360

acccaggtca ccgtctcctc a                                              381
```

```
<210> SEQ ID NO 37
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 0A08 1B08 0A07 1E05 0H12 1H07 1E03 0F09 4D01
      0D12 Consensus CDR1
<220> FEATURE:
<221> NAME/KEY: MISC_FEATURE
<222> LOCATION: (3)..(3)
<223> OTHER INFORMATION: Xaa = Thr or Ser
<220> FEATURE:
<221> NAME/KEY: MISC_FEATURE
<222> LOCATION: (6)..(6)
<223> OTHER INFORMATION: Xaa = Val or Lys

<400> SEQUENCE: 37

Gly Arg Xaa Phe Ser Xaa Lys Pro
1               5


<210> SEQ ID NO 38
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 0A08 1B08 0A07 1E05 0H12 1H07 1E03 0F09 4D01
      0D12 Consensus CDR2
<220> FEATURE:
<221> NAME/KEY: MISC_FEATURE
<222> LOCATION: (3)..(3)
<223> OTHER INFORMATION: Xaa = Phe or Tyr

<400> SEQUENCE: 38

Ala Ser Xaa Thr Gly Val Ser Thr
1               5


<210> SEQ ID NO 39
<211> LENGTH: 20
<212> TYPE: PRT
<213> ORGANISM: Vicugna pacos
<220> FEATURE:
<221> NAME/KEY: MISC_FEATURE
<222> LOCATION: (1)..(20)
<223> OTHER INFORMATION: 0A08 1B08 0A07 1E05 0H12 1H07 1E03 0F09 4D01
      0D12 Consensus CDR3
<220> FEATURE:
<221> NAME/KEY: MISC_FEATURE
<222> LOCATION: (4)..(4)
<223> OTHER INFORMATION: Xaa = Thr or Leu
<220> FEATURE:
<221> NAME/KEY: MISC_FEATURE
<222> LOCATION: (15)..(15)
<223> OTHER INFORMATION: Xaa = Val or Arg
<220> FEATURE:
<221> NAME/KEY: MISC_FEATURE
<222> LOCATION: (16)..(16)
```

-continued

<223> OTHER INFORMATION: Xaa = Leu or Arg

<400> SEQUENCE: 39

```
Ala Gly Thr Xaa Arg Thr Leu Trp Gly Ser Lys Trp Arg Asp Xaa Xaa
1               5                   10                  15

Glu Tyr Glu Tyr
            20
```

<210> SEQ ID NO 40
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 4F10 1E08 3B04 4F12 CDR1

<400> SEQUENCE: 40

```
Gly Leu Asp Phe Ser Ser Tyr Ala
1               5
```

<210> SEQ ID NO 41
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 4F10 1E08 3B04 4F12 CDR2

<400> SEQUENCE: 41

```
Ile Ser Arg Phe Gly Gly Arg Leu
1               5
```

<210> SEQ ID NO 42
<211> LENGTH: 16
<212> TYPE: PRT
<213> ORGANISM: Vicugna pacos
<220> FEATURE:
<221> NAME/KEY: MISC_FEATURE
<223> OTHER INFORMATION: 4F10 1E08 3B04 4F12 CDR3

<400> SEQUENCE: 42

```
Ala Ala Asp Arg Arg Ser Gly Leu Gly Thr Ser Lys Glu Tyr Asp Tyr
1               5                   10                  15
```

<210> SEQ ID NO 43
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 2A09 1G06 CDR1

<400> SEQUENCE: 43

```
Gly Ile Ile Phe Ser Ile Asn Ala
1               5
```

<210> SEQ ID NO 44
<211> LENGTH: 7
<212> TYPE: PRT
<213> ORGANISM: Vicugna pacos
<220> FEATURE:
<221> NAME/KEY: MISC_FEATURE
<222> LOCATION: (1)..(7)
<223> OTHER INFORMATION: 2A09 1G06 CDR2

<400> SEQUENCE: 44

Ile Ser Ala Tyr Asp His Thr
1 5

<210> SEQ ID NO 45
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 2A09 1G06 CDR3

<400> SEQUENCE: 45

Asn Val Asp Glu Ile Arg Lys Phe
1 5

<210> SEQ ID NO 46
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 0A09 CDR1

<400> SEQUENCE: 46

Gly Arg Ser Phe Ser Leu Tyr Gly
1 5

<210> SEQ ID NO 47
<211> LENGTH: 9
<212> TYPE: PRT
<213> ORGANISM: Vicugna pacos
<220> FEATURE:
<221> NAME/KEY: MISC_FEATURE
<222> LOCATION: (1)..(9)
<223> OTHER INFORMATION: 0A09 CDR2

<400> SEQUENCE: 47

Ile Ser Gly Ser Gly Leu Ala Thr Ser
1 5

<210> SEQ ID NO 48
<211> LENGTH: 18
<212> TYPE: PRT
<213> ORGANISM: Vicugna pacos
<220> FEATURE:
<221> NAME/KEY: MISC_FEATURE
<222> LOCATION: (1)..(18)
<223> OTHER INFORMATION: 0A09 CDR3

<400> SEQUENCE: 48

Ala Gln Arg Trp Thr Ser Gly Thr Ile Ala Arg Ala Thr Gly Glu Tyr
1 5 10 15

Gly Tyr

<210> SEQ ID NO 49
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 4C10 CDR1

<400> SEQUENCE: 49

Gly Ser Ile Phe Ser Gly Asp Ala
1 5

<210> SEQ ID NO 50
<211> LENGTH: 7
<212> TYPE: PRT
<213> ORGANISM: Vicugna pacos
<220> FEATURE:
<221> NAME/KEY: MISC_FEATURE
<222> LOCATION: (1)..(7)
<223> OTHER INFORMATION: 4C10 CDR2

<400> SEQUENCE: 50

Ile Gly Lys Glu Gly Asp Thr
1 5

<210> SEQ ID NO 51
<211> LENGTH: 13
<212> TYPE: PRT
<213> ORGANISM: Vicugna pacos
<220> FEATURE:
<221> NAME/KEY: MISC_FEATURE
<222> LOCATION: (1)..(13)
<223> OTHER INFORMATION: 4C10 CDR3

<400> SEQUENCE: 51

Ala Thr Phe Glu Glu Arg Pro Gln Pro Ser Tyr Val Tyr
1 5 10

<210> SEQ ID NO 52
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 0A08 1B08 0A07 0H12 0F09 CDR1

<400> SEQUENCE: 52

Gly Arg Thr Phe Ser Val Lys Pro
1 5

<210> SEQ ID NO 53
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 0A08 1B08 0A07 1E05 0H12 1E03 0F09 CDR2

<400> SEQUENCE: 53

Ala Ser Phe Thr Gly Val Ser Thr
1 5

<210> SEQ ID NO 54
<211> LENGTH: 20
<212> TYPE: PRT
<213> ORGANISM: Vicugna pacos
<220> FEATURE:
<221> NAME/KEY: MISC_FEATURE
<222> LOCATION: (1)..(20)
<223> OTHER INFORMATION: 0A08 1B08 0A07 0H12 1H07 0F09 4D01 0D12 CDR3

<400> SEQUENCE: 54

Ala Gly Thr Thr Arg Thr Leu Trp Gly Ser Lys Trp Arg Asp Val Leu
1 5 10 15

Glu Tyr Glu Tyr

20

<210> SEQ ID NO 55
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 1E05 1E03 CDR1

<400> SEQUENCE: 55

Gly Arg Ser Phe Ser Val Lys Pro
1 5

<210> SEQ ID NO 56
<211> LENGTH: 20
<212> TYPE: PRT
<213> ORGANISM: Vicugna pacos
<220> FEATURE:
<221> NAME/KEY: MISC_FEATURE
<222> LOCATION: (1)..(20)
<223> OTHER INFORMATION: 1E05 1E03 CDR3

<400> SEQUENCE: 56

Ala Gly Thr Leu Arg Thr Leu Trp Gly Ser Lys Trp Arg Asp Arg Arg
1 5 10 15

Glu Tyr Glu Tyr
20

<210> SEQ ID NO 57
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 1H07 4D01 0D12 CDR1

<400> SEQUENCE: 57

Gly Arg Thr Phe Ser Lys Lys Pro
1 5

<210> SEQ ID NO 58
<211> LENGTH: 8
<212> TYPE: PRT
<213> ORGANISM: Vicugna pacos
<220> FEATURE:
<221> NAME/KEY: MISC_FEATURE
<222> LOCATION: (1)..(8)
<223> OTHER INFORMATION: 1H07 4D01 0D12 CDR2

<400> SEQUENCE: 58

Ala Ser Tyr Thr Gly Val Ser Thr
1 5

<210> SEQ ID NO 59
<211> LENGTH: 38
<212> TYPE: DNA
<213> ORGANISM: Artificial Sequence
<220> FEATURE:
<223> OTHER INFORMATION: PCR amplification forward primer

<400> SEQUENCE: 59
tatgaagaca ccaggcccag gtaaagctgg aggagtct 38

<210> SEQ ID NO 60

-continued

```
<211> LENGTH: 30
<212> TYPE: DNA
<213> ORGANISM: Artificial Sequence
<220> FEATURE:
<223> OTHER INFORMATION: PCR amplification reverse primer

<400> SEQUENCE: 60

ttgttcggat cctgaggaga cggtgacctg                                        30
```